United States Patent
Morse et al.

(10) Patent No.: US 6,800,440 B2
(45) Date of Patent: Oct. 5, 2004

(54) ROLE OF PPH1 GENE IN PULMONARY HYPERTENSION

(75) Inventors: Jane H. Morse, Bronx, NY (US); James A. Knowles, Rowaytn, CT (US)

(73) Assignee: The Trustees of Columbia University in the City of New York, New York, NY (US)

( * ) Notice: Subject to any disclaimer, the term of this patent is extended or adjusted under 35 U.S.C. 154(b) by 0 days.

(21) Appl. No.: 09/904,380

(22) Filed: Jul. 12, 2001

(65) Prior Publication Data

US 2002/0022229 A1 Feb. 21, 2002

Related U.S. Application Data

(60) Provisional application No. 60/217,773, filed on Jul. 12, 2000.

(51) Int. Cl.$^7$ .............................. C12Q 1/68; G01N 33/53
(52) U.S. Cl. .............................................. 435/6; 435/7.1
(58) Field of Search ....................... 435/6, 7.1

(56) References Cited

U.S. PATENT DOCUMENTS 6,291,206 B1 * 9/2001 Wozney et al. ............ 435/69.1
6,306,622 B1 * 10/2001 Rosenbaum et al. ....... 435/69.1
6,642,002 B2 * 11/2003 Loyd et al. .................... 435/6
2002/0102576 A1 * 8/2002 Loyd et al. .................... 435/6

FOREIGN PATENT DOCUMENTS

WO         02/06534    *   1/2002    ............ C12Q/1/68

* cited by examiner

Primary Examiner—Kenneth R. Horlick
(74) Attorney, Agent, or Firm—John P. White; Cooper & Dunham LLP

(57) ABSTRACT

This invention provides a method of detecting whether a subject is either predisposed to or afflicted with a pulmonary disease which comprises (1) obtaining a suitable sample from the subject; (2) detecting in the sample a bone morphogenetic protein receptor-II mutation which is not present in wildtype bone morphogenetic protein receptor-II, wherein the presence of a mutation indicates that the subject is predisposed to or afflicted with the pulmonary disease. In one embodiment, the pulmonary disease is Familial Primary Pulmonary Hypertension.

5 Claims, 9 Drawing Sheets

Figure 1-1

| EXON (SIZE) | EXON 3' | | INTRON (SIZE) | | EXON 5' | |
|---|---|---|---|---|---|---|
| EXON 1 (>460 bp) | GCT G | gtgagtagtccggc.. | intron 1 (>30 kb) | ..tttcctttatttag | CT TCG | |
| | Ala A | | | | la Ser | |
| EXON 2 (171 bp) | CAA G | gcaagtgatacttc.. | intron 2 (~2.3 kb) | ..catattgatttatag | GA TAT | |
| | Gln G | | | | ly Cys | |
| EXON 3 (171 bp) | CTC A | gtaagtaaagtaacc.. | intron 3 (>30 kb) | ..tttgtttctttag | GT CCA | |
| | Leu S | | | | er Pro | |
| EXON 4 (111 bp) | ACA G | gtaaaaattaccatt.. | intron 4 (~3.8 kb) | ..ttcctgttcttatag | GA GAC | |
| | Thr G | | | | ly Asp | |
| EXON 5 (92 bp) | TTG GAG | gtaagtttgcgtta.. | intron 5 (~6 kb) | ..ttaaaacacttgcag | CTG ATT | |
| | Leu Glu | | | | Leu Ile | |
| EXON 6 (231 bp) | CCC AAT | gtaagttcttcatag.. | intron 6 (~4.1 kb) | ..ttttcctctatatag | GGA TCT | |
| | Pro Asn | | | | Gly Ser | |
| EXON 7 (115 bp) | GGA G | gtaagatagtcaata.. | intron 7 (>7 kb) | ..aaattatccaaacag | AT CAT | |
| | Gly A | | | | sp His | |
| EXON 8 (161 bp) | AGC GAG | gtgagtgtatacaaa.. | intron 8 (~1.6 kb) | ..actcaatttatcag | GTT GGC | |
| | Ser Glu | | | | Val Gly | |
| EXON 9 (148 bp) | CCA G | gtaaaaactactgtc.. | intron 9 (>9.7 kb) | ..tcacaaatccacag | GG GAA | |
| | Pro G | | | | ly Glu | |
| EXON 10 (137 bp) | AGC CTG | gtaagaaaaactaa.. | intron 10 (>5 kb) | ..tactttgtcttacag | GCA GTG | |
| | Ser Leu | | | | Ala Val | |
| EXON 11 (173 bp) | GAA CG | gtaagaccctaggg.. | intron 11 (>20 kb) | ..ctttcttcttttag | C AAC | |

Figure 1-2

```
EXON 12 (1280 bp)  Glu Ar
                   CAG A    gtaagtgagggatc..  intron 12 (~1.8 kb)  ..cactttatttcag   g Asn
                   Gln I                                                             TA GGT
EXON 13 (>251 bp)                                                                    le Gly
```

Figure 3

```
R491W                              LKETIEDCWDQDAEA W LTAQCAEERMAEL
                                                 491
BMPR-II [Homo sapiens]             LKETIEDCWDQDAEA R LTAQCAEERMAEL
BMPR-II [Mus musculus]             LKETIEDCWDQDAEA R LTAQCAEERMAEL
BMPR-II [Xenopus laevis]           LKETIDDCWDQDAEA R LTAQCAEERMAEL
BMPR-II [Gallus gallus]            LKETIEDCWDQDAEA R LTAQCAEERMAEL
TGFR-II [Homo sapiens]             VCETLTECWDHDPEA R LTAQCVAERFSEL
TGFR-II [Mus musculus]             VCETLTECWDHDPEA R LTAQCVAERFSEL
TGFR-II [Rattus Norvegicus]        VCETLTECWDHDAEA R LTAQCVAERFSEL
ActR-II [Homo sapiens]             LCVTIEDCWDHDAEA R LSAGCVEERVSLI
ActR-II [sheep]                    LCETIEECWDHDAEA R LSAGCVGERITQM
ActR-II [Gallus gallus]            LCETIEECWDHDAEA R LSAGCVEERIIQM
AMHR-II [Homo sapiens]             LRELLEDCWDADPEA R LTAECVQQRLAAL
AMHR-II [Rattus norvegicus]        LRELLEDCWDADPEA R LTAECVQQRLAAL
DAF4 [C.elegans]                   LKKVTEEMWDPEACA R ITAGCAFARVWNH
XSTK3 [Xenopus laevis]             LCVTIEECWDHDAEA R LSAGCVEERISQI
Consensus                          LKETIEDCWD DAEA R LTAQCVEERMAEL
```

Figure 4

| Family # | #A/#C/#U | Exon # | DNA Sequence Variation | Protein Sequence Variation |
|---|---|---|---|---|
| PPH001, 008 and 021 | 4/5/13 | 11 | 1471C>T | R491W |
| PPH010 | 2/0/1 | 8 | 1099-1103delGGGGA | E368fsX1 |
| PPH015 | 6/1/8 | 12 | 2579delT | N861fsX10 |
| PPH017 | 3/0/6 | 4 | 507-510delCTTTinsAAA | C169X |
| PPH018 | 3/2/4 | 12 | 2617C>T | R873X |
| PPH019 | 1/0/5* | 11 | 1472G>A | R491Q |
| PPH022 | 2/0/0 | 6 | 690-691delAGinsT | K230fsX21 |
| PPH011 | | 9 | 1248-1251delATTT | F417X |
| PPH012 | | 8 | 994C>T | R332X |
| PPH013 | | 3 | 295T>C | C99R |
| PPH028 | | 8 | 1097delG | P366fsX8 |
| PPH032 | | 6 | 727G>T | E243X |
| PPH037 | | 9 | 1214delA | D405fsX6 |
| PPH042 | | 12 | 2441-2442delAC | H814fsX2 |
| PPH047 | | 12 | 2695C>T | R899X |
| M552 | | 2 | 189-209del21 | Del 64-70(STCYGLW) |
| PPH045 | | 3 | 296G>A | C99Y |
| PPH052 | | 3 | 250T>C | C84R |
| PPH67-6701 | | 8 | 1040G>A | C347Y |

Figure 5-1

```
 +1    Met Thr Ser Ser Leu Gln Arg Pro Trp Arg Val Pro Trp Leu Pro Trp Thr
   1   ATGACTTCCT CGCTGCAGCG GCCCTGGCGG GTGCCCTGGC TACCATGGAC
       TACTGAAGGA GCGACGTCGC CGGGACCGCC CACGGGACCG ATGGTACCTG
 +1    Thr Ile Leu Leu Val Ser Thr Ala Ala Ala Ser Gln Asn Gln Glu Arg Leu Cys
  51   CATCCTGCTG GTCAGCACTG CGGCTGCTTC GCAGAATCAA GAACGGCTAT
       GTAGGACGAC CAGTCGTGAC GCCGACGAAG CGTCTTAGTT CTTGCCGATA
 +1    Cys Ala Phe Lys Asp Pro Tyr Gln Gln Asp Leu Gly Ile Gly Glu Ser Arg
 101   GTGCGTTTAA AGATCCGTAT CAGCAAGACC TTGGGATAGG TGAGAGTAGA
       CACGCAAATT TCTAGGCATA GTCGTTCTGG AACCCTATCC ACTCTCATCT
 +1    Ile Ser His Glu Asn Gly Thr Ile Leu Cys Ser Lys Gly Ser Thr Cys Tyr
 151   ATCTCTCATG AAAATGGGAC AATATTATGC TCGAAAGGTA GCACCTGCTA
       TAGAGAGTAC TTTTACCCTG TTATAATACG AGCTTTCCAT CGTGGACGAT
 +1    Tyr Gly Leu Trp Glu Lys Ser Lys Gly Asp Ile Asn Leu Val Lys Gln Gly Cys
 201   TGGCCTTTGG GAGAAATCAA AAGGGGACAT AAATCTTGTA AAACAAGGAT
       ACCGGAAACC CTCTTTAGTT TTCCCCTGTA TTTAGAACAT TTTGTTCCTA
 +1    Cys Trp Ser His Ile Gly Asp Pro Gln Glu Cys His Tyr Glu Glu Cys Val
 251   GTTGGTCTCA CATTGGAGAT CCCCAAGAGT GTCACTATGA AGAATGTGTA
       CAACCAGAGT GTAACCTCTA GGGGTTCTCA CAGTGATACT TCTTACACAT
 +1    Val Thr Thr Thr Pro Pro Ser Ile Gln Asn Gly Thr Tyr Arg Phe Cys Cys
 301   GTAACTACCA CTCCTCCCTC AATTCAGAAT GGAACATACC GTTTCTGCTG
       CATTGATGGT GAGGAGGGAG TTAAGTCTTA CCTTGTATGG CAAAGACGAC
 +1    Cys Cys Ser Thr Asp Leu Cys Asn Val Asn Phe Thr Glu Asn Phe Pro Pro Pro
 351   TTGTAGCACA GATTTATGTA ATGTCAACTT TACTGAGAAT TTTCCACCTC
       AACATCGTGT CTAAATACAT TACAGTTGAA ATGACTCTTA AAAGGTGGAG
 +1    Pro Asp Thr Thr Pro Leu Ser Pro Pro His Ser Phe Asn Arg Asp Glu Thr
 401   CTGACACAAC ACCACTCAGT CCACCTCATT CATTTAACCG AGATGAGACA
       GACTGTGTTG TGGTGAGTCA GGTGGAGTAA GTAAATTGGC TCTACTCTGT
 +1    Ile Ile Ile Ala Leu Ala Ser Val Ser Val Leu Ala Val Leu Ile Val Ala
 451   ATAATCATTG CTTTGGCATC AGTCTCTGTA TTAGCTGTTT TGATAGTTGC
       TATTAGTAAC GAAACCGTAG TCAGAGACAT AATCGACAAA ACTATCAACG
 +1    Ala Leu Cys Phe Gly Tyr Arg Met Leu Thr Gly Asp Arg Lys Gln Gly Leu His
 501   CTTATGCTTT GGATACAGAA TGTTGACAGG AGACCGTAAA CAAGGTCTTC
       GAATACGAAA CCTATGTCTT ACAACTGTCC TCTGGCATTT GTTCCAGAAG
 +1    His Ser Met Asn Met Met Glu Ala Ala Ala Ser Glu Pro Ser Leu Asp Leu
 551   ACAGTATGAA CATGATGGAG GCAGCAGCAT CCGAACCCTC TCTTGATCTA
       TGTCATACTT GTACTACCTC CGTCGTCGTA GGCTTGGGAG AGAACTAGAT
 +1    Asp Asn Leu Lys Leu Leu Glu Leu Ile Gly Arg Gly Arg Tyr Gly Ala Val
 601   GATAATCTGA AACTGTTGGA GCTGATTGGC CGAGGTCGAT ATGGAGCAGT
       CTATTAGACT TTGACAACCT CGACTAACCG GCTCCAGCTA TACCTCGTCA
 +1    Val Tyr Lys Gly Ser Leu Asp Glu Arg Pro Val Ala Val Lys Val Phe Ser Phe
 651   ATATAAAGGC TCCTTGGATG AGCGTCCAGT TGCTGTAAAA GTGTTTTCCT
       TATATTTCCG AGGAACCTAC TCGCAGGTCA ACGACATTTT CACAAAAGGA
 +1    Phe Ala Asn Arg Gln Asn Phe Ile Asn Glu Lys Asn Ile Tyr Arg Val Pro
 701   TTGCAAACCG TCAGAATTTT ATCAACGAAA AGAACATTTA CAGAGTGCCT
       AACGTTTGGC AGTCTTAAAA TAGTTGCTTT TCTTGTAAAT GTCTCACGGA
 +1    Leu Met Glu His Asp Asn Ile Ala Arg Phe Ile Val Gly Asp Glu Arg Val
 751   TTGATGGAAC ATGACAACAT TGCCCGCTTT ATAGTTGGAG ATGAGAGAGT
       AACTACCTTG TACTGTTGTA ACGGGCGAAA TATCAACCTC TACTCTCTCA
```

Figure 5-2

```
      +1  Val Thr Ala Asp Gly Arg Met Glu Tyr Leu Leu Val Met Glu Tyr Tyr Pro Asn
 801      CACTGCAGAT GGACGCATGG AATATTTGCT TGTGATGGAG TACTATCCCA
          GTGACGTCTA CCTGCGTACC TTATAAACGA ACACTACCTC ATGATAGGGT
      +1  Asn Gly Ser Leu Cys Lys Tyr Leu Ser Leu His Thr Ser Asp Trp Val Ser
 851      ATGGATCTTT ATGCAAGTAT TTAAGTCTCC ACACAAGTGA CTGGGTAAGC
          TACCTAGAAA TACGTTCATA AATTCAGAGG TGTGTTCACT GACCCATTCG
      +1  Ser Cys Arg Leu Ala His Ser Val Thr Arg Gly Leu Ala Tyr Leu His Thr
 901      TCTTGCCGTC TTGCTCATTC TGTTACTAGA GGACTGGCTT ATCTTCACAC
          AGAACGGCAG AACGAGTAAG ACAATGATCT CCTGACCGAA TAGAAGTGTG
      +1  Thr Glu Leu Pro Arg Gly Asp His Tyr Lys Pro Ala Ile Ser His Arg Asp Leu
 951      AGAATTACCA CGAGGAGATC ATTATAAACC TGCAATTTCC CATCGAGATT
          TCTTAATGGT GCTCCTCTAG TAATATTTGG ACGTTAAAGG GTAGCTCTAA
      +1  Leu Asn Ser Arg Asn Val Leu Val Lys Asn Asp Gly Thr Cys Val Ile Ser
1001      TAAACAGCAG AAATGTCCTA GTGAAAAATG ATGGAACCTG TGTTATTAGT
          ATTTGTCGTC TTTACAGGAT CACTTTTTAC TACCTTGGAC ACAATAATCA
      +1  Asp Phe Gly Leu Ser Met Arg Leu Thr Gly Asn Arg Leu Val Arg Pro Gly
1051      GACTTTGGAC TGTCCATGAG GCTGACTGGA AATAGACTGG TGCGCCCAGG
          CTGAAACCTG ACAGGTACTC CGACTGACCT TTATCTGACC ACGCGGGTCC
      +1  Gly Glu Glu Asp Asn Ala Ala Ile Ser Glu Val Gly Thr Ile Arg Tyr Met Ala
1101      GGAGGAAGAT AATGCAGCCA TAAGCGAGGT TGGCACTATC AGATATATGG
          CCTCCTTCTA TTACGTCGGT ATTCGCTCCA ACCGTGATAG TCTATATACC
      +1  Ala Pro Glu Val Leu Glu Gly Ala Val Asn Leu Arg Asp Cys Glu Ser Ala
1151      CACCAGAAGT GCTAGAAGGA GCTGTGAACT TGAGGGACTG TGAATCAGCT
          GTGGTCTTCA CGATCTTCCT CGACACTTGA ACTCCCTGAC ACTTAGTCGA
      +1  Leu Lys Gln Val Asp Met Tyr Ala Leu Gly Leu Ile Tyr Trp Glu Ile Phe
1201      TTGAAACAAG TAGACATGTA TGCTCTTGGA CTAATCTATT GGGAGATATT
          AACTTTGTTC ATCTGTACAT ACGAGAACCT GATTAGATAA CCCTCTATAA
      +1  Phe Met Arg Cys Thr Asp Leu Phe Pro Gly Glu Ser Val Pro Glu Tyr Gln Met
1251      TATGAGATGT ACAGACCTCT TCCCAGGGGA ATCCGTACCA GAGTACCAGA
          ATACTCTACA TGTCTGGAGA AGGGTCCCCT TAGGCATGGT CTCATGGTCT
      +1  Met Ala Phe Gln Thr Glu Val Gly Asn His Pro Thr Phe Glu Asp Met Gln
1301      TGGCTTTTCA GACAGAGGTT GGAAACCATC CCACTTTTGA GGATATGCAG
          ACCGAAAAGT CTGTCTCCAA CCTTTGGTAG GGTGAAAACT CCTATACGTC
      +1  Val Leu Val Ser Arg Glu Lys Gln Arg Pro Lys Phe Pro Glu Ala Trp Lys
1351      GTTCTCGTGT CTAGGGAAAA ACAGAGACCC AAGTTCCCAG AAGCCTGGAA
          CAAGAGCACA GATCCCTTTT TGTCTCTGGG TTCAAGGGTC TTCGGACCTT
      +1  Lys Glu Asn Ser Leu Ala Val Arg Ser Leu Lys Glu Thr Ile Glu Asp Cys Trp
1401      AGAAAATAGC CTGGCAGTGA GGTCACTCAA GGAGACAATC GAAGACTGTT
          TCTTTTATCG GACCGTCACT CCAGTGAGTT CCTCTGTTAG CTTCTGACAA
      +1  Trp Asp Gln Asp Ala Glu Ala Arg Leu Thr Ala Gln Cys Ala Glu Glu Arg
1451      GGGACCAGGA TGCAGAGGCT CGGCTTACTG CACAGTGTGC TGAGGAAAGG
          CCCTGGTCCT ACGTCTCCGA GCCGAATGAC GTGTCACACG ACTCCTTTCC
      +1  Met Ala Glu Leu Met Met Ile Trp Glu Arg Asn Lys Ser Val Ser Pro Thr
1501      ATGGCTGAAC TTATGATGAT TTGGGAAAGA AACAAATCTG TGAGCCCAAC
          TACCGACTTG AATACTACTA AACCCTTTCT TTGTTTAGAC ACTCGGGTTG
      +1  Thr Val Asn Pro Met Ser Thr Ala Met Gln Asn Glu Arg Asn Leu Ser His Asn
1551      AGTCAATCCA ATGTCTACTG CTATGCAGAA TGAACGCAAC CTGTCACATA
          TCAGTTAGGT TACAGATGAC GATACGTCTT ACTTGCGTTG GACAGTGTAT
```

Figure 5-3

```
      +1  Asn Arg Arg Val Pro Lys Ile Gly Pro Tyr Pro Asp Tyr Ser Ser Ser Ser
    1601  ATAGGCGTGT GCCAAAAATT GGTCCTTATC CAGATTATTC TTCCTCCTCA
          TATCCGCACA CGGTTTTTAA CCAGGAATAG GTCTAATAAG AAGGAGGAGT
      +1  Tyr Ile Glu Asp Ser Ile His His Thr Asp Ser Ile Val Lys Asn Ile Ser
    1651  TACATTGAAG ACTCTATCCA TCATACTGAC AGCATCGTGA AGAATATTTC
          ATGTAACTTC TGAGATAGGT AGTATGACTG TCGTAGCACT TCTTATAAAG
      +1  Ser Ser Glu His Ser Met Ser Ser Thr Pro Leu Thr Ile Gly Glu Lys Asn Arg
    1701  CTCTGAGCAT TCTATGTCCA GCACACCTTT GACTATAGGG GAAAAAAACC
          GAGACTCGTA AGATACAGGT CGTGTGGAAA CTGATATCCC CTTTTTTTGG
      +1  Arg Asn Ser Ile Asn Tyr Glu Arg Gln Gln Ala Gln Ala Arg Ile Pro Ser
    1751  GAAATTCAAT TAACTATGAA CGACAGCAAG CACAAGCTCG AATCCCCAGC
          CTTTAAGTTA ATTGATACTT GCTGTCGTTC GTGTTCGAGC TTAGGGGTCG
      +1  Pro Glu Thr Ser Val Thr Ser Leu Ser Thr Asn Thr Thr Thr Thr Asn Thr
    1801  CCTGAAACAA GTGTCACCAG CCTCTCCACC AACACAACAA CCACAAACAC
          GGACTTTGTT CACAGTGGTC GGAGAGGTGG TTGTGTTGTT GGTGTTTGTG
      +1  Thr Thr Gly Leu Thr Pro Ser Thr Gly Met Thr Thr Ile Ser Glu Met Pro Tyr
    1851  CACAGGACTC ACGCCAAGTA CTGGCATGAC TACTATATCT GAGATGCCAT
          GTGTCCTGAG TGCGGTTCAT GACCGTACTG ATGATATAGA CTCTACGGTA
      +1  Tyr Pro Asp Glu Thr Asn Leu His Thr Thr Asn Val Ala Gln Ser Ile Gly
    1901  ACCCAGATGA AACAAATCTG CATACCACAA ATGTTGCACA GTCAATTGGG
          TGGGTCTACT TTGTTTAGAC GTATGGTGTT TACAACGTGT CAGTTAACCC
      +1  Pro Thr Pro Val Cys Leu Gln Leu Thr Glu Glu Asp Leu Glu Thr Asn Lys
    1951  CCAACCCCTG TCTGCTTACA GCTGACAGAA GAAGACTTGG AAACCAACAA
          GGTTGGGGAC AGACGAATGT CGACTGTCTT CTTCTGAACC TTTGGTTGTT
      +1  Lys Leu Asp Pro Lys Glu Val Asp Lys Asn Leu Lys Glu Ser Ser Asp Glu Asn
    2001  GCTAGACCCA AAAGAAGTTG ATAAGAACCT CAAGGAAAGC TCTGATGAGA
          CGATCTGGGT TTTCTTCAAC TATTCTTGGA GTTCCTTTCG AGACTACTCT
      +1  Asn Leu Met Glu His Ser Leu Lys Gln Phe Ser Gly Pro Asp Pro Leu Ser
    2051  ATCTCATGGA GCACTCTCTT AAACAGTTCA GTGGCCCAGA CCCACTGAGC
          TAGAGTACCT CGTGAGAGAA TTTGTCAAGT CACCGGGTCT GGGTGACTCG
      +1  Ser Thr Ser Ser Ser Leu Leu Tyr Pro Leu Ile Lys Leu Ala Val Glu Ala
    2101  AGTACTAGTT CTAGCTTGCT TTACCCACTC ATAAAACTTG CAGTAGAAGC
          TCATGATCAA GATCGAACGA AATGGGTGAG TATTTTGAAC GTCATCTTCG
      +1  Ala Thr Gly Gln Gln Asp Phe Thr Gln Thr Ala Asn Gly Gln Ala Cys Leu Ile
    2151  AACTGGACAG CAGGACTTCA CACAGACTGC AAATGGCCAA GCATGTTTGA
          TTGACCTGTC GTCCTGAAGT GTGTCTGACG TTTACCGGTT CGTACAAACT
      +1  Ile Pro Asp Val Leu Pro Thr Gln Ile Tyr Pro Leu Pro Lys Gln Gln Asn
    2201  TTCCTGATGT TCTGCCTACT CAGATCTATC CTCTCCCCAA GCAGCAGAAC
          AAGGACTACA AGACGGATGA GTCTAGATAG GAGAGGGGTT CGTCGTCTTG
      +1  Leu Pro Lys Arg Pro Thr Ser Leu Pro Leu Asn Thr Lys Asn Ser Thr Lys
    2251  CTTCCCAAGA GACCTACTAG TTTGCCTTTG AACACCAAAA ATTCAACAAA
          GAAGGGTTCT CTGGATGATC AAACGGAAAC TTGTGGTTTT TAAGTTGTTT
      +1  Lys Glu Pro Arg Leu Lys Phe Gly Ser Lys His Lys Ser Asn Leu Lys Gln Val
    2301  AGAGCCCCGG CTAAAATTTG GCAGCAAGCA CAAATCAAAC TTGAAACAAG
          TCTCGGGGCC GATTTTAAAC CGTCGTTCGT GTTTAGTTTG AACTTTGTTC
      +1  Val Glu Thr Gly Val Ala Lys Met Asn Thr Ile Asn Ala Ala Glu Pro His
    2351  TCGAAACTGG AGTTGCCAAG ATGAATACAA TCAATGCAGC AGAACCTCAT
          AGCTTTGACC TCAACGGTTC TACTTATGTT AGTTACGTCG TCTTGGAGTA
```

Figure 5-4

```
        +1   Val Val Thr Val Thr Met Asn Gly Val Ala Gly Arg Asn His Ser Val Asn
      2401   GTGGTGACAG TCACCATGAA TGGTGTGGCA GGTAGAAACC ACAGTGTTAA
             CACCACTGTC AGTGGTACTT ACCACACCGT CCATCTTTGG TGTCACAATT
        +1   Asn Ser His Ala Ala Thr Thr Gln Tyr Ala Asn Arg Thr Val Leu Ser Gly Gln
      2451   CTCCCATGCT GCCACAACCC AATATGCCAA TAGGACAGTA CTATCTGGCC
             GAGGGTACGA CGGTGTTGGG TTATACGGTT ATCCTGTCAT GATAGACCGG
        +1   Gln Thr Thr Asn Ile Val Thr His Arg Ala Gln Glu Met Leu Gln Asn Gln
      2501   AAACAACCAA CATAGTGACA CATAGGGCCC AAGAAATGTT GCAGAATCAG
             TTTGTTGGTT GTATCACTGT GTATCCCGGG TTCTTTACAA CGTCTTAGTC
        +1   Phe Ile Gly Glu Asp Thr Arg Leu Asn Ile Asn Ser Ser Pro Asp Glu His
      2551   TTTATTGGTG AGGACACCCG GCTGAATATT AATTCCAGTC CTGATGAGCA
             AAATAACCAC TCCTGTGGGC CGACTTATAA TTAAGGTCAG GACTACTCGT
        +1   His Glu Pro Leu Leu Arg Arg Glu Gln Gln Ala Gly His Asp Glu Gly Val Leu
      2601   TGAGCCTTTA CTGAGACGAG AGCAACAAGC TGGCCATGAT GAAGGTGTTC
             ACTCGGAAAT GACTCTGCTC TCGTTGTTCG ACCGGTACTA CTTCCACAAG
        +1   Leu Asp Arg Leu Val Asp Arg Arg Glu Arg Pro Leu Glu Gly Gly Arg Thr
      2651   TGGATCGTCT TGTGGACAGG AGGGAACGGC CACTAGAAGG TGGCCGAACT
             ACCTAGCAGA ACACCTGTCC TCCCTTGCCG GTGATCTTCC ACCGGCTTGA
        +1   Asn Ser Asn Asn Asn Asn Ser Asn Pro Cys Ser Glu Gln Asp Val Leu Ala
      2701   AATTCCAATA ACAACAACAG CAATCCATGT TCAGAACAAG ATGTTCTTGC
             TTAAGGTTAT TGTTGTTGTC GTTAGGTACA AGTCTTGTTC TACAAGAACG
        +1   Ala Gln Gly Val Pro Ser Thr Ala Ala Asp Pro Gly Pro Ser Lys Pro Arg Arg
      2751   ACAGGGTGTT CCAAGCACAG CAGCAGATCC TGGGCCATCA AAGCCCAGAA
             TGTCCCACAA GGTTCGTGTC GTCGTCTAGG ACCCGGTAGT TTCGGGTCTT
        +1   Arg Ala Gln Arg Pro Asn Ser Leu Asp Leu Ser Ala Thr Asn Val Leu Asp
      2801   GAGCACAGAG GCCTAATTCT CTGGATCTTT CAGCCACAAA TGTCCTGGAT
             CTCGTGTCTC CGGATTAAGA GACCTAGAAA GTCGGTGTTT ACAGGACCTA
        +1   Gly Ser Ser Ile Gln Ile Gly Glu Ser Thr Gln Asp Gly Lys Ser Gly Ser
      2851   GGCAGCAGTA TACAGATAGG TGAGTCAACA CAAGATGGCA AATCAGGATC
             CCGTCGTCAT ATGTCTATCC ACTCAGTTGT GTTCTACCGT TTAGTCCTAG
        +1   Ser Gly Glu Lys Ile Lys Lys Arg Val Lys Thr Pro Tyr Ser Leu Lys Arg Trp
      2901   AGGTGAAAAG ATCAAGAAAC GTGTGAAAAC TCCCTATTCT CTTAAGCGGT
             TCCACTTTTC TAGTTCTTTG CACACTTTTG AGGGATAAGA GAATTCGCCA
        +1   Trp Arg Pro Ser Thr Trp Val Ile Ser Thr Glu Ser Leu Asp Cys Glu Val
      2951   GGCGCCCCTC CACCTGGGTC ATCTCCACTG AATCGCTGGA CTGTGAAGTC
             CCGCGGGGAG GTGGACCCAG TAGAGGTGAC TTAGCGACCT GACACTTCAG
        +1   Asn Asn Asn Gly Ser Asn Arg Ala Val His Ser Lys Ser Ser Thr Ala Val
      3001   AACAATAATG GCAGTAACAG GGCAGTTCAT TCCAAATCCA GCACTGCTGT
             TTGTTATTAC CGTCATTGTC CCGTCAAGTA AGGTTTAGGT CGTGACGACA
        +1   Val Tyr Leu Ala Glu Gly Gly Thr Ala Thr Thr Met Val Ser Lys Asp Ile Gly
      3051   TTACCTTGCA GAAGGAGGCA CTGCTACAAC CATGGTGTCT AAAGATATAG
             AATGGAACGT CTTCCTCCGT GACGATGTTG GTACCACAGA TTTCTATATC
        +1   Gly Met Asn Cys Leu ---
      3101   GAATGAACTG TCTGTGA
             CTTACTTGAC AGACACT
```

ROLE OF PPH1 GENE IN PULMONARY HYPERTENSION

This application is a continuation-in-part and claims the benefit of U.S. Provisional Application No. 60/217,773, filed Jul. 12, 2000, the contents of which are hereby incorporated by reference into this application.

The invention disclosed herein was made with Government support under NIH Grant No. HL60056-02 from the National Heart, Lung and Blood Institute. Accordingly, the government has certain rights in this invention.

Throughout this application, various publications are referenced within parentheses. Disclosures of these publications in their entireties are hereby incorporated by reference into this application to more fully describe the state of the art to which this invention pertains. Full bibliographic citations for these references may be found immediately preceding the claims.

BACKGROUND OF THE INVENTION

Familial Primary Pulmonary Hypertension (PPH, MIM 178600) is a rare (1 in $10^5$ to $10^6$) autosomal dominant disorder with reduced penetrance that has been mapped to a 3-centimorgan region on chromosome 2q34 (PPH1 locus) (Morse et al. 1996; Morse et al. 1997; Nichols et al. 1997; Deng et al. 2000). It is characterized by monoclonal plexiform lesions of proliferating endothelial cells in pulmonary arterioles (Lee et al. 1998) that lead to elevated pulmonary artery pressures, right ventricular failure, and death (Rich et al. 1987). The disease can occur from infancy throughout life with a mean age of onset of 36 years and has a 2:1 ratio of affected females to males. Without intervention, the median survival is less than three years after diagnosis (D'Alonzo et al. 1991), although recent advances, such as long-term prostacyclin therapy (Barst et al. 1996) and transplantation (Pasque et al. 1995) have significantly improved the quality of life and survival in some patients. Although FPPH is rare, cases secondary to known etiologies are more common and include those associated with the appetite suppressant drugs, including phentermine-fenfluramine (Douglas et al. 1981; Abenhaim et al. 1996).

SUMMARY OF THE INVENTION

This invention provides a method of detecting whether a subject is either predisposed to or afflicted with a pulmonary disease which comprises (1) obtaining a suitable sample from the subject; (2) detecting in the sample a bone morphogenetic protein receptor-II mutation which is not present in wildtype bone morphogenetic protein receptor-II, wherein the presence of a mutation indicates that the subject is predisposed to or afflicted with the pulmonary disease.

This invention provides a method of detecting whether a subject is either predisposed to or afflicted with a pulmonary disease which comprises:

a) obtaining a suitable nucleic acid sample from the subject; and
b) detecting in the nucleic acid the presence of a mutation in a gene which encodes bone morphogenetic protein receptor-II, wherein the presence of a mutation indicates that the subject is predisposed to or afflicted with the pulmonary disease.

In one embodiment of the subject invention, the pulmonary disease is Primary Pulmonary Hypertension. In one embodiment of the subject invention, the Primary Pulmonary Hypertension is Familial Primary Pulmonary Hypertension.

This invention provides a method of predicting an increased likelihood of a subject's giving birth to twins or triplets which comprises:

a) obtaining a suitable nucleic acid sample from the subject;
b) detecting the presence of one copy of a mutant gene which encodes bone morphogenetic protein receptor-II, thereby indicating that the subject is heterozygous for the mutation, wherein heterozygosity predicts an increased likelihood of the subject giving birth to twins or triplets.

This invention provides a method of predicting an increased likelihood of a subject having a miscarriage prior to giving birth to a child which comprises:

a) obtaining a suitable nucleic acid sample from the subject;
b) detecting the presence of two copies of a mutant gene which encodes bone morphogenetic protein receptor-II, thereby indicating that the subject is homozygous for the mutation, wherein homozygosity predicts an increased likelihood of the subject having a miscarriage prior to giving birth to a child.

This invention provides a method of preventing and/or treating Familial Primary Pulmonary Hypertension in a subject which comprises introducing a nucleic acid comprising a gene encoding wildtype bone morphogenetic protein receptor-II protein into a suitable cell under conditions such that the nucleic acid expresses the wildtype bone morphogenetic protein receptor-II protein so as to thereby prevent and/or treat Familial Primary Pulmonary Hypertension in the subject.

This invention provides a method of preventing and/or treating Familial Primary Pulmonary Hypertension in a subject which comprises administering to the subject an amount of wildtype bone morphogenetic protein receptor-II effective to prevent and/or treat Familial Primary Pulmonary Hypertension so as to thereby prevent and/or treat Familial Primary Pulmonary Hypertension in the subject.

This invention provides a method of detecting whether a subject is either predisposed to or afflicted with Familial Primary Pulmonary Hypertension which comprises:

a) obtaining a suitable nucleic acid sample from the subject; and
b) detecting the presence of a $(GGC)_{12}$ trinucleotide repeat at the 5' end of the bone morphogenetic protein receptor-II gene at positions 928 to 963, wherein the presence of the trinucleotide repeat indicates that the subject is either predisposed to or afflicted with Familial Primary Pulmonary Hypertension.

This invention provides a method of screening for a compound capable of treating Familial Primary Pulmonary Hypertension which comprises:

a) contacting a cell which expresses a mutant bone morphogenetic protein receptor-II with the compound; and
b) determining whether the compound is capable of reversing the functional deficit in Familial Primary Pulmonary Hypertension, wherein a reversal of the functional deficit indicates that the compound is capable of treating Familial Primary Pulmonary Hypertension.

This invention provides a method of obtaining a composition which comprises:

a) identifying a compound capable of treating Familial Primary Pulmonary Hypertension by the above method; and
b) admixing the compound so identified or a homolog or derivative thereof with a carrier.

This invention provides a transgenic animal which comprises a mutation in a gene which encodes a bone morphogenetic protein receptor-II.

BRIEF DESCRIPTION OF THE FIGURES

FIGS. 1-1 to 1-2

Figure 2:
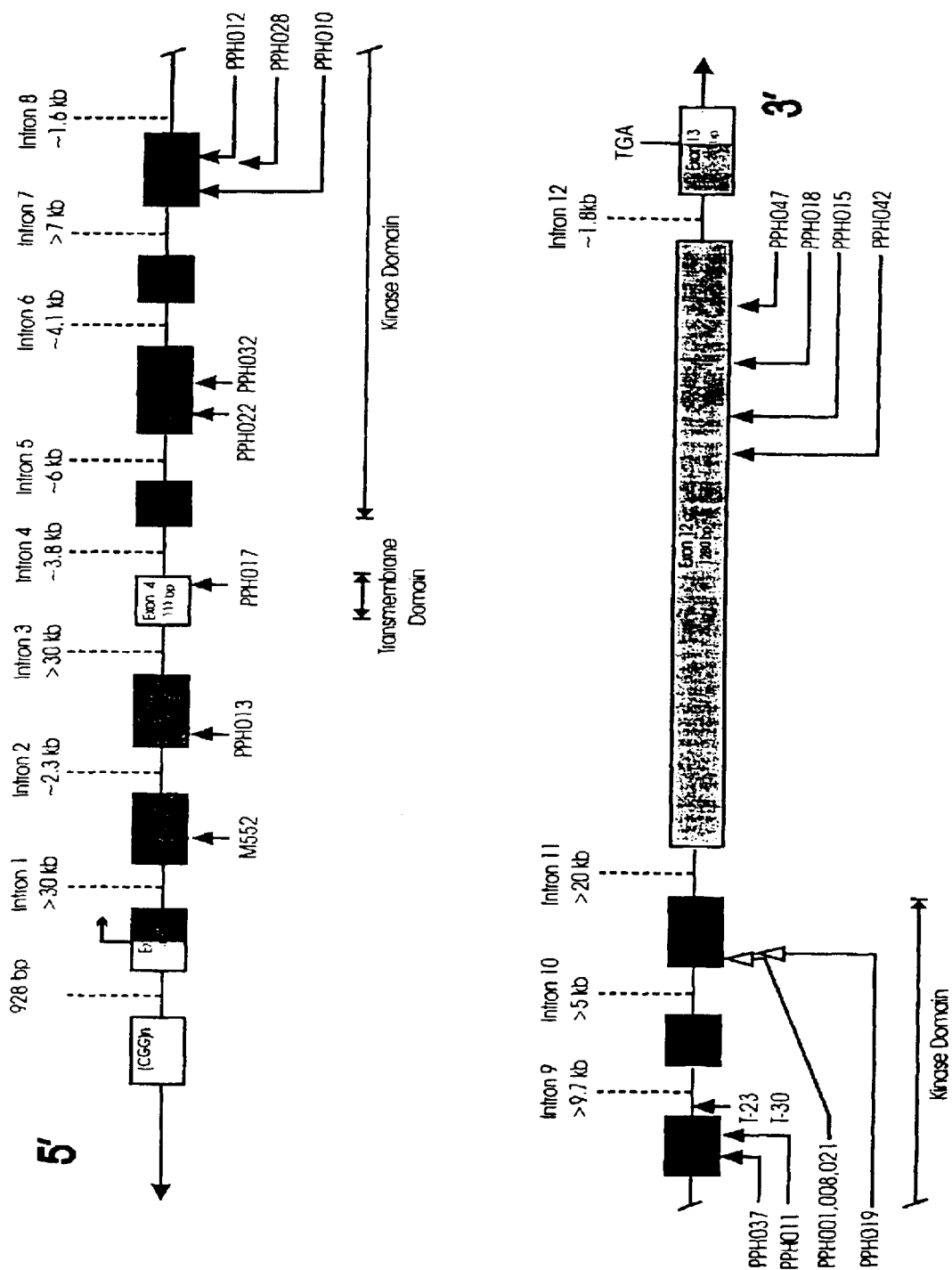

Intron/Exon boundaries of the human BMPR2 gene. The nucleotide sequence of all intron/exon boundaries and the known size of each exon and approximate size of each intron are shown. (SEQ ID Nos.:3–14).

FIG. 2

Intron/Exon structure of the human BMPR2 gene. Intron and exon sizes are as indicated. Mutations that cause premature termination of BMPR2 are shown as closed arrows. Open arrows indicate mutations in Arg491. The transmembrane and kinase domains are encoded by the indicated exons.

FIG. 3

Sequence alignment of the type-II TGF-b superfamily receptors surrounding R491 in BMPR-II. The mutation in families PPH001, 008 and 021 was aligned with all known type-II receptors (over 50) and 14 of these are displayed. Abbrevations: BMPR-II, bone morphogenetic protein type II receptor; TGFR-II, transforming growth factor beta receptor type II; ActR-II, Activin receptor type II; AMHR-II, anti-mullerian hormone type II receptor; DAF-4, development regulatory growth factor-4; XSTK3, Xenopus activin receptor. (SEQ ID NOS:15–30).

FIG. 4

BMPR2 mutations observed in PPH. DNA sequences are referenced to GENEBANK BMPR2 CDNA sequence number NM_001204. These sequences are also set forth in FIG. 5. #A/#C/#U is the number of affected known carrier or unaffected individuals in each family or set of families. Nomenclature: fs denotes a frameshift mutation; Xl denotes a one amino acid tail after the frameshift.

FIGS. 5-1 to 5-4

Nucleic acid and amino acid sequences for wildtype BMPR2. The nucleic acid sequence is also set forth in SEQ ID NO:1. The amino acid sequence is also set forth in SEQ ID NO:2.

DETAILED DESCRIPTION OF THE INVENTION

This invention provides a method of detecting whether a subject is either predisposed to or afflicted with a pulmonary disease which comprises (1) obtaining a suitable sample from the subject; (2) detecting in the sample a bone morphogenetic protein receptor-II mutation which is not present in wildtype bone morphogenetic protein receptor-II, wherein the presence of a mutation indicates that the subject is predisposed to or afflicted with the pulmonary disease.

In one embodiment, the suitable sample is a nucleic acid sample, and the mutation is detected in a nucleic acid encoding bone morphogenetic protein receptor-II. In one embodiment, the suitable sample is one which comprises a bone morphogenetic protein receptor-II polypeptide, and the mutation is detected in the bone morphogenetic protein receptor-II polypeptide.

In one embodiment, the suitable sample is a nucleic acid sample. Accordingly, one may detect a mutation in the nucleic acid. Such nucleic acid may be a DNA or RNA. In one embodiment, the sample is a protein or polypeptide sample. Accordingly, one may detect a mutation in the encoded protein or polypeptide. For example, one may detect a mutation in bone morphogenetic protein receptor-II polypeptide, such as a mutation in the amino acid sequence.

This invention provides a method of detecting whether a subject is either predisposed to or afflicted with a pulmonary disease which comprises:

a) obtaining a suitable nucleic acid sample from the subject; and
b) detecting in the nucleic acid the presence of a mutation in a gene which encodes bone morphogenetic protein receptor-II, wherein the presence of a mutation indicates that the subject is predisposed to or afflicted with the pulmonary disease.

One skilled in the art would know various methods for detecting a mutation on the nucleic acid level. For example, one may use a nucleic acid probe which binds to a target nucleic acid. Such nucleic acid probe may be one which is detectable. For example, the detectable nucleic acid may be labeled with a detectable marker. Such markers include but are not limited to a radioactive, a calorimetric, a luminescent, and a fluorescent label. For example, the probe may be specific for a sequence having a particular mutation (such as one of the mutations described herein), such that it is capable of detecting a mutant nucleic acid. Alternatively, the probe may specific for a corresponding wildtype sequence for a particular mutation, such that it is capable of detecting a wildtype nucleic acid (i.e. one which is wildtype with respect to the mutation).

In various embodiments, the nucleic acid probe included but is not limited to nucleic acids which are at least 5, nucleotides in length, at least 10, nucleotides in length, at least 15, nucleotides in length, at least 20 nucleotides in length, at least 25 nucleotides in length, an at least 30 nucleotides in length. The subject invention also encompasses other lengths of nucleic acid probes. In one embodiment the nucleic acid and/or nucleic acid probe is DNA. In another embodiment the nucleic acid and/or nucleic acid probe is RNA.

One skilled in the art would know various conditions under which the hybridization may take place. For example, high stringency hybridization conditions may be selected at about 5° C. lower than the thermal melting point ($T_m$) for the specific sequence at a defined ionic strength and pH. The $T_m$ is the temperature (under defined ionic strength and pH) at which 50% of the salt concentration is at least about 0.02 molar at pH 7 and the temperature is at least about 60° C. As other factors may significantly affect the stringency of hybridization, including, among others, base composition and size of the complementary strands, the presence of organic solvents, i.e. salt or formamide concentration, and the extent of base mismatching, the combination of parameters is more important than the absolute measure of any one. For example, high stringency may be attained by overnight hybridization at about 68° C. in a 6× SSC solution, washing at room temperature with 6× SSC solution, followed by washing at about 68° C. in a 0.6× SSC solution.

Hybridization with moderate stringency may be attained for example by: 1) filter pre-hybridizing and hybridizing with a solution of 3× SSC, 50% formamide, 0.1M Tris buffer at pH 7.5, 5× Denhardt's solution; 2.) pre-hybridization at 37° C. for 4 hours; 3) hybridization at 37° C. with amount of labeled probe equal to 3,000,000 cpm total for 16 hours; 4) wash in 4× SSC and 0.1% SDS solution; 5) wash 4× for 1 minute each at room temperature in 4× SSC at 60° C. for 30 minutes each; and 6) dry and expose to film.

Nucleic acid probe technology is well known to those skilled in the art who readily appreciate that such probes may vary greatly in length and may be labeled with a detectable label, such as a radioisotope or fluorescent dye, to facilitate detection of the probe. DNA probe molecules may be produced by insertion of a DNA molecule having the full-length or a fragment of the isolated nucleic acid molecule of the DNA virus into suitable vectors, such as plasmids or bacteriophages, followed by transforming into suitable bacterial host cells, replication in the transformed bacterial host cells and harvesting of the DNA probes, using methods well known in the art. Alternatively, probes may be generated chemically from DNA synthesizers.

RNA probes may be generated by inserting the full length or a fragment of the isolated nucleic acid molecule of the DNA virus downstream of a bacteriophage promoter such as T3, T7 or SP6. Large amounts of RNA probe may be produced by incubating the labeled nucleotides with a linearized isolated nucleic acid molecule of the DNA virus or its fragment where it contains an upstream promoter in the presence of the appropriate RNA polymerase.

As defined herein nucleic acid probes may be DNA or RNA fragments. DNA fragments can be prepared, for example, by digesting plasmid DNA, or by use of PCR, or synthesized by either the phosphoramidite method described by Beaucage and Carruthers, 1981, *Tetrahedron Lett.* 22, 1859–1862 or by the triester method according to Matteucci et al., 1981, *Am. Chem. Soc.* 103:3185. A double stranded fragment may then be obtained, if desired, by annealing the chemically synthesized single strands together under appropriate conditions or by synthesizing the complementary strand using DNA polymerase with an appropriate primer sequence. Where a specific sequence for a nucleic acid probe is given, it is understood that the complementary strand is also identified and included. The complementary strand will work equally well in situations where the target is a double-stranded nucleic acid. It is also understood that when a specific sequence is identified for use a nucleic probe, a subsequence of the listed sequence which is 25 base pairs (bp) or more in length is also encompassed for use as a probe.

Another way to detect a mutation on the nucleic acid level is to perform nucleic acid sequencing on the nucleic acid sample obtained from the subject. For example, one may perform DNA sequencing to detect the presence of the mutation. One skilled in the art know how to sequence a particular nucleic acid. Examples of such sequencing methods include The Maxam and Gilbert method and the Sanger method, both of which are described in Recombinant DNA, Second Edition by James Watson et al (1992), Scientific American Books the contents of which are hereby incorporated by reference.

If a particular mutation results in the gain and/or loss of particular restriction cleavage sites, one may also perform a restriction digest on the nucleic acid to determine if a particular mutation is present.

On may also detect a mutation at the polypeptide or protein level. This invention provides a method of detecting whether a subject is either predisposed to or afflicted with a pulmonary disease which comprises:

a) obtaining a suitable sample of bone morphogenetic protein receptor-II polypeptide from the subject; and
b) detecting the presence of a mutation in the bone morphogenetic protein receptor-II polypeptide, wherein the presence of a mutation indicates that the subject is predisposed to or afflicted with the pulmonary disease.

For example, may use a detectable antibody capable of binding to an epitope which is present in the mutant protein but not present in the wildtype protein. The binding of the antibody to the protein indicates a mutant protein and therefore, that the subject is predisposed to or afflicted with the pulmonary disease. One may use a detectable antibody capable of binding to an epitope which is present in the wildtype protein but not present in the mutant protein. Binding of the antibody to the protein indicates a wildtype protein.

If a mutation results in a nonconservative mutation, such as a positively charged amino acid for a negatively charged amino acid, such mutation may be identified by running the protein in a gel to determine a difference in charge. One skilled in the art would know how to identify a nonconservative mutation.

For mutations which result in truncated proteins, such as the introduction of a stop codon or a frameshift mutation which results in a truncation, such mutations may be identified by detecting the truncated protein, such as by running the protein on a gel and determining its size based on the distance that it moves within the gel.

In one embodiment, the pulmonary disease is Primary Pulmonary Hypertension. In one embodiment of the subject invention, the Primary Pulmonary Hypertension is Familial Primary Pulmonary Hypertension.

As used herein, "subject" means any animal or artificially modified animal. The subjects include but are mot limited to a human being, a primate, an equine, an opine, an avian, a bovine, a porcine, a canine, a feline or a mouse. Artificially modified animals include, but are not limited to, SCID mice with human immune systems. The animals include but are not limited to mice, rats, dogs, guinea pigs, ferrets, rabbits, and primates. In the preferred embodiment, the subject is a human being.

In one embodiment, a bone morphogenetic protein receptor-II polypeptide is encoded by a gene which is located on chromosome 2q34.

In one embodiment, a wildtype nucleic acid encoding a bone morphogenetic protein receptor-II polypepetide comprises consecutive nucleotides comprising the nucleic acid sequence set forth in SEQ ID NO: 1.

In one embodiment, a wildtype bone morphogenetic protein receptor-II polypeptide comprises consecutive amino acids comprising the amino acid sequence set forth in SEQ ID NO: 2.

In one embodiment, the mutation results in a truncated bone morphogenetic protein receptor-II.

In one embodiment, the mutated nucleic acid comprises a deletion of a nucleotide segment guanosine-guanosineguanosine-guanosine-adenosine located at positions 1099–1103 in a wildtype nucleic acid, which wildtype nucleic acid comprises the sequence set forth in SEQ ID NO:1. In one embodiment, the mutated bone morphogenetic protein receptor-II polypeptide comprises a frameshift mutation at a glutamic acid residue located at position 368 in the wildtype polypeptide, which wildtype polypeptide comprises the amino acid sequence set forth in SEQ ID NO:2. As exemplified in FIG. 4, in one embodiment, the mutant protein has an amino acid tail which is one amino acid in length from the mutation at position 368, i.e. such mutant protein is terminated or truncated one amino acid from the frameshift mutation.

In one embodiment, the mutated nucleic acid comprises a deletion of a thymidine residue located at position 2579 in a wildtype nucleic acid, which wildtype nucleic acid comprises the sequence set forth in SEQ ID NO:1. In one embodiment, the mutated bone morphogenetic protein receptor-II polypeptide comprises a frameshift mutation at an asparagine residue located at position 861 in the wildtype polypeptide, which wildtype polypeptide comprises the amino acid sequence set forth in SEQ ID NO:2. As exemplified in FIG. 4, in one embodiment, the mutant protein has an amino acid tail which is ten amino acids in length from the mutation at position 861, i.e. such mutant protein is terminated or truncated ten amino acids from the frameshift mutation.

In one embodiment, the mutated nucleic acid comprises a replacement of a nucleotide segment cytosine-thymidine-thymidine-thymidine located at positions 507–510 in a wildtype nucleic acid with a nucleotide segment adenosine-adenosine-adenosine, which wildtype nucleic acid comprises the sequence set forth in SEQ ID NO:1. In one embodiment, the mutated bone morphogenetic protein receptor-II polypeptide comprises a mutation of a cysteine located at position 169 in a wildtype polypeptide to a termination codon, which wildtype polypeptide comprises the sequence set forth in SEQ ID NO:2. Such mutation is exemplified in FIG. 4.

In one embodiment, the mutated nucleic acid comprises a mutation of a cytosine located at position number 2617 in a wildtype nucleic acid to a thymidine, which wildtype nucleic acid comprises the sequence set forth in SEQ ID NO:1. In one embodiment, the mutated bone morphogenetic protein receptor-II polypeptide comprises a mutation of an arginine located at position 873 in a wiltype polypeptide to a termination codon, which wildtype polypeptide comprises the sequence set forth in SEQ ID NO:2. Such mutation is exemplified in FIG. 4.

In one embodiment, the mutated nucleic acid comprises a replacement of a nucleotide segment adenosine-guanosine present at positions 690–691 in a wildtype nucleic acid with a thymidine residue, which wildtype nucleic acid comprises the sequence set forth in SEQ ID NO:1. In one embodiment, the mutated bone morphogenetic protein receptor-II polypeptide comprises a frameshift mutation at a lysine residue located at position 230 in a wildtype polypeptide, which wildtype polypeptide comprises the sequence set forth in SEQ ID NO:2. As exemplified in FIG. 4, in one embodiment, the mutant protein has an amino acid tail which is twenty one amino acids in length from the mutation at position 230, i.e. such mutant protein is terminated or truncated twenty one amino acids from the frameshift mutation.

In one embodiment, the mutation is a missense mutation.

In one embodiment, the mutated nucleic acid comprises a mutation of a cytosine located at position number 1471 in a wildtype nucleic acid to a thymidine, which wildtype nucleic acid comprises the sequence set forth in SEQ ID NO:1. In one embodiment, the mutated bone morphogenetic protein receptor-II polypeptide comprises a mutation of an arginine located at position 491 in a wildtype polypeptide to a tryptophan, which wildtype polypeptide has the sequence set forth in SEQ ID NO:2. Such mutation is exemplified in FIG. 4.

In one embodiment, the mutated nucleic acid comprises a mutation of a auanosine located at position number 1472 in a wildtype nucleic acid to an adenosine, which wildtype nucleic acid comprises the sequence set forth in SEQ ID NO:1. In one embodiment, the mutated bone morphogenetic protein receptor-II polypepetide comprises a mutation of an arginine located at position number 491 in a wildtype polypeptide to a glutamine, which wildtype polypeptide has the sequence set forth in SEQ ID NO:2. Such mutation is exemplified in FIG. 4.

In one embodiment, the mutated nucleic acid comprises a deletion of a nucleotide segment adenosine-thymidine-thymidine-thymidine located at positions 1248–1251 in a wildtype nucleic acid, which wildtype nucleic acid comprises the sequence set forth in SEQ ID NO:1. In one embodiment, the mutated bone morphogenetic protein receptor-II polypepetide comprises a mutation of an phenylalanine located at position number 417 in a wildtype polypeptide to a stop codon, which wildtype polypeptide has the sequence set forth in SEQ ID NO:2. Such mutation is exemplified in FIG. 4.

In one embodiment, the mutated nucleic acid comprises a mutation of a cytosine located at position number 994 in a wildtyne nucleic acid to a thymidine, which wildtype nucleic acid comprises the sequence set forth in SEQ ID NO:1. In one embodiment, the mutated bone morphogenetic protein receptor-II polypepetide comprises a mutation of an arginine located at position number 332 in a wildtype polypeptide to a stop codon, which wildtype polypeptide has the sequence set forth in SEQ ID NO:2.

In one embodiment, the mutated nucleic acid comprises a mutation of a thymidine located at position number 295 in a wildtype nucleic acid to a cytosine, which wildtype nucleic acid comprises the sequence set forth in SEQ ID NO:1. In one embodiment, the mutated bone morphogenetic protein receptor-II polypepetide comprises a mutation of a cysteine located at position number 99 in a wildtype polypeptide to an arginine, which wildtype polypeptide has the sequence set forth in SEQ ID NO:2.

In one embodiment, the mutated nucleic acid comprises a deletion of a guanosine residue located at position 1097 in a wildtype nucleic acid, which wildtype nucleic acid comprises the sequence set forth in Seq ID NO:1. In one embodiment, the mutated bone morphogenetic protein receptor-II polypeptide comprises a frameshift mutation at a proline residue located at position 366 in the wildtype polypeptide, which wildtype polypeptide comprises the amino acid sequence set forth in SEQ ID NO:2. As exemplified in FIG. 4, in one embodiment, the mutant protein has an amino acid tail which is 8 amino acids in length from the mutation at position 366, i.e. such mutant protein is terminated or truncated 8 amino acids from the frameshift mutation.

In one embodiment, the mutated nucleic acid comprises a mutation of a guanosine located at position number 727 in a wildtype nucleic acid to a thymidine, which wildtype nucleic acid comprises the sequence set forth in SEQ ID NO:1. In one embodiment, the mutated bone morphogenetic protein receptor-II polypepetide comprises a mutation of a glutamic acid located at position number 243 in a wildtype polypeptide to a stop codon, which wildtype polypeptide has the sequence set forth in SEQ ID NO:2.

In one embodiment, the mutated nucleic acid comprises a deletion of an adenosine residue located at position 1214 in a wildtype nucleic acid, which wildtype nucleic acid comprises the sequence set forth in Seq ID NO:1. In one embodiment, the mutated bone morphogenetic protein receptor-II polypeptide comprises a frameshift mutation at an aspartic acid residue located at position 405 in the wildtype polypeptide, which wildtype polypeptide comprises the amino acid sequence set forth in SEQ ID NO:2. As exemplified in FIG. 4, in one embodiment, the mutant protein has an amino acid tail which is 6 amino acids in length from the mutation at position 405, i.e. such mutant protein is terminated or truncated 6 amino acids from the frameshift mutation.

In one embodiment, the mutated nucleic acid comprises a deletion of a nucleotide segment adenosine-cytosine located at positions 2441–2442 in a wildtype nucleic acid, which wildtype nucleic acid comprises the sequence set forth in SEQ ID NO:1. In one embodiment, the mutated bone morphogenetic protein receptor-II polypeptide comprises a frameshift mutation at a histidine residue located at position 814 in the wildtype polypeptide, which wildtype polypeptide comprises the amino acid sequence set forth in SEQ ID NO:2. As exemplified in FIG. 4, in one embodiment, the mutant protein has an amino acid tail which is 2 amino acids in length from the mutation at position 814, i.e. such mutant protein is terminated or truncated 2 amino acids from the frameshift mutation.

In one embodiment, the mutated nucleic acid comprises a mutation of a cytosine located at position number 2695 in a wildtype nucleic acid to a thymidine, which wildtype nucleic acid comprises the sequence set forth in SEQ ID NO:1. In one embodiment, the mutated bone morphogenetic protein receptor-II polypepetide comprises a mutation of an arginine located at position number 899 in a wildtype polypeptide to a stop codon, which wildtype polypeptide has the sequence set forth in SEQ ID NO:2.

In one embodiment, the mutated nucleic acid comprises a deletion of a nucleotide segment present at positions 189–209 in a wildtype nucleic acid, which wildtype nucleic acid comprises the sequence set forth in SEQ ID NO:1. In one embodiment, the mutated bone morphogenetic protein receptor-II polypepetide comprises a deletion of an amino acid segment serine-threonine-cysteine-tyrosine-glycine-leucine-tryptophan located at position numbers 64–70 in a wildtype polypeptide, which wildtype polypeptide has the sequence set forth in SEQ ID NO:2.

In one embodiment, the mutated nucleic acid comprises a mutation of a guanosine located at position number 296 in a wildtype nucleic acid to a adenosine, which wildtype nucleic acid comprises the sequence set forth in SEQ ID NO:1. In one embodiment, the mutated bone morphogenetic protein receptor-II polypepetide comprises a mutation of a cysteine located at position number 99 in a wildtype polypeptide to a tyrosine, which wildtype polypeptide has the sequence set forth in SEQ ID NO:2.

In one embodiment, the mutated nucleic acid comprises a mutation of a thymidine located at position number 250 in a wildtype nucleic acid to a cytosine, which wildtype nucleic acid comprises the sequence set forth in SEQ ID NO:1. In one embodiment, the mutated bone morphogenetic protein receptor-II polypepetide comprises a mutation of a cysteine located at position number 84 in a wildtype polypeptide to an arginine, which wildtype polypeptide has the sequence set forth in SEQ ID NO:2.

In one embodiment, the mutated nucleic acid comprises a mutation of a guanosine located at position number 1040 in a wildtype nucleic acid to a adenosine, which wildtype nucleic acid comprises the sequence set forth in SEQ ID NO:1. In one embodiment, the mutated bone morphogenetic protein receptor-II polypepetide comprises a mutation of a cysteine located at position number 347 in a wildtype polypeptide to a tyrosine, which wildtype polypeptide has the sequence set forth in SEQ ID NO:2.

As used herein, the following standard abbreviations are used throughout the specification to indicate specific amino acids: A=ala=alanine; R=arg=arginine; N=asn=asparagine D=asp=aspartic acid; C=cys=cysteine; Q=gln=glutamine; E=glu=glutamic acid; G=gly=glycine; H=his=histidine; I=ile=isoleucine; L=leu=leucine; K=lys=lysine; M=met= methionine; F=phe=phenylalanine; P=pro=proline; S=ser= serine; T=thr=threonine; W=trp=tryptophan; Y=tyr= tyrosine; and V=val=valine.

As used herein, the following standard abbreviations are used throughout the specification to indicate specific nucleotides: C=cytosine; A=adenosine; T=thymidine; and G=guanosine.

In one embodiment, the invention comprises detecting at least one of the mutations described herein. In one embodiment, the invention comprises detecting at least two of the mutations described herein. In one embodiment, the invention comprises detecting at least three of the mutations described herein. In one embodiment, the invention comprises detecting at least four of the mutations described herein. In one embodiment, the invention comprises detecting at least five of the mutations described herein. In one embodiment, the invention comprises detecting at least six of the mutations described herein. In one embodiment, the invention comprises detecting at least seven of the mutations described herein.

One skilled in the art would know various methods for detecting a mutation described herein in the subject.

In one embodiment of the subject invention, the subject is suffering from an asthmatic symptom, so as to thereby prevent a subject afflicted with Familial Primary Pulmonary Hypertension from being misdiagnosed as asthmatic.

In one embodiment of the subject invention, the asthmatic symptom is wheezing or intermittent shortness of breath.

This invention provides a method of predicting an increased likelihood of a subject giving birth to twins or triplets which comprises:
  a) obtaining a suitable nucleic acid sample from the subject;
  b) detecting the presence of one copy of a mutant nucleic acid which encodes a bone morphogenetic protein receptor-II polypeptide, thereby indicating that the subject is heterozygous for the mutation,
wherein heterozygosity predicts an increased likelihood of the subject giving birth to twins or triplets.

This invention provides a method of predicting an increased likelihood of a subject having a miscarriage prior to giving birth to a child which comprises:
  a) obtaining a suitable nucleic acid sample from the subject;
  b) detecting the presence of two copies of a mutant nucleic acid which encodes a bone morphogenetic protein receptor-II polypeptide, thereby indicating that the subject is homozygous for the mutation,
wherein homozygosity predicts an increased likelihood of the subject having a miscarriage prior to giving birth to a child.

This invention provides a method of preventing and/or treating Familial Primary Pulmonary Hypertension in a subject which comprises introducing a nucleic acid comprising a gene encoding wildtype bone morphogenetic protein receptor-II protein into a suitable cell under conditions such that the nucleic acid expresses the wildtype bone morphogenetic protein receptor-II protein so as to thereby prevent and/or treat Familial Primary Pulmonary Hypertension in the subject. This invention provides a method of preventing and/or treating Familial Primary Pulmonary Hypertension in a subject which comprises introducing a nucleic acid encoding a wildtype bone morphogenetic protein receptor-II polypeptide operably linked to a promotor into a suitable cell under conditions such that the nucleic acid expresses the wildtype bone morphogenetic protein receptor-II protein so as to thereby prevent and/or treat Familial Primary Pulmonary Hypertension in the subject. In one embodiment of the subject invention, the suitable cell is a lung cell.

As used herein, "treating" means either slowing, stopping or reversing the progression of the disorder. In the preferred embodiment, "treating" means reversing the progression to the point of eliminating the disorder. As used herein, "preventing" means that the subject will not become afflicted with the disorder.

In one embodiment, a vector comprises the nucleic acid. Vectors which may be used in the methods of the present invention are viral including adenoviruses, retroviral, vectors, adeno-associated viral (AAV) vectors.

The viral vector selected should meet the following criteria: 1) the vector must be able to infect the cell of interest and thus viral vectors having an appropriate host range must be selected; 2) the transferred gene should be capable of persisting and being expressed in a cell for an extended period of time; and 3) the vector should be safe to the host and cause minimal cell transformation. Retroviral vectors and adenoviruses offer an efficient, useful, and presently the best-characterized means of introducing and expressing foreign genes efficiently in mammalian cells. These vectors have very broad host and cell type ranges, express genes stably and efficiently. The safety of these vectors has been proved by many research groups. In fact many are in clinical trials.

Other virus vectors that may be used for gene transfer into cells for correction of disorders include retroviruses such as Moloney murine leukemia virus (MoMuLV); papovaviruses such as JC, SV40, polyoma, adenoviruses; Epstein-Barr Virus (EBV); papilloma viruses, e.g. bovine papilloma virus type I (BPV); vaccinia and poliovirus and other human and animal viruses.

Adenoviruses have several properties that make them attractive as cloning vehicles (Bachettis et al.: Transfer of gene for thymidine kinase-deficient human cells by purified herpes simplex viral DNA. PNAS USA, 1977 74:1590; Berkner, K. L.: Development of adenovirus vectors for expression of heterologous genes. Biotechniques, 1988 6:616; Ghosh-Choudhury G., et al., Human adenovirus cloning vectors based on infectious bacterial plasmids. Gene 1986; 50:161; Hag-Ahmand Y., et al., Development of a helper-independent human adenovirus vector and its use in the transfer of the herpes simplex virus thymidine kinase gene. J Virol 1986; 57:257; Rosenfeld M., et al., Adenovirus-mediated transfer of a recombinant alpha.sub.1-antitrypsin gene to the lung epithelium in vivo. Science 1991; 252:431).

For example, adenoviruses possess an intermediate sized genome that replicates in cellular nuclei; many serotypes are clinically innocuous; adenovirus genomes appear to be stable despite insertion of foreign genes; foreign genes appear to be maintained without loss or rearrangement; and adenoviruses can be used as high level transient expression vectors with an expression period up to 4 weeks to several months. Extensive biochemical and genetic studies suggest that it is possible to substitute up to 7–7.5 kb of heterologous sequences for native adenovirus sequences generating viable, conditional, helper-independent vectors (Kaufman R. J.; identification of the component necessary for adenovirus translational control and their utilization in cDNA expression vectors. PNAS USA, 1985 82:689).

AAV is a small human parvovirus with a single stranded DNA genome of approximately 5 kb. This virus can be propagated as an integrated provirus in several human cell types. AAV vectors have several advantage for human gene therapy. For example, they are trophic for human cells but can also infect other mammalian cells; (2) no disease has been associated with AAV in humans or other animals; (3) integrated AAV genomes appear stable in their host cells; (4) there is no evidence that integration of AAV alters expression of host genes or promoters or promotes their rearrangement; (5) introduced genes can be rescued from the host cell by infection with a helper virus such as adenovirus.

HSV-1 vector system facilitates introduction of virtually any gene into non-mitotic cells (Geller et al. an efficient deletion mutant packaging system for a defective herpes simplex virus vectors: Potential applications to human gene therapy and neuronal physiology. PNAS USA, 1990 87:8950).

Another vector for mammalian gene transfer is the bovine papilloma virus-based vector (Sarver N, et al., Bovine papilloma virus DNA: A novel eukaryotic cloning vector. Mol Cell Biol 1981; 1:486).

Vaccinia and other poxvirus-based vectors provide a mammalian gene transfer system. Vaccinia virus is a large double-stranded DNA virus of 120 kilodaltons (kd) genomic size (Panicali D, et al., Construction of poxvirus as cloning vectors: Insertion of the thymidine kinase gene from herpes simplex virus into the DNA of infectious vaccine virus. Proc Natl Acad Sci USA 1982; 79:4927; Smith et al. infectious vaccinia virus recombinants that express hepatitis B virus surface antigens. Nature, 1983 302:490.)

Retroviruses are packages designed to insert viral genes into host cells (Guild B, et al., Development of retrovirus vectors useful for expressing genes in cultured murine embryonic cells and hematopoietic cells in vivo. J Virol 1988; 62:795; Hock R. A., et al., Retrovirus mediated transfer and expression of drug resistance genes in human hemopoietic progenitor cells. Nature 1986; 320:275).

The basic retrovirus consists of two identical strands of RNA packaged in a proviral protein. The core surrounded by a protective coat called the envelope, which is derived from the membrane of the previous host but modified with glycoproteins contributed by the virus.

Markers and amplifiers can also be employed in the subject expression systems. A variety of markers are known which are useful in selecting for transformed cell lines and generally comprise a gene whose expression confers a selectable phenotype on transformed cells when the cells are grown in an appropriate selective medium. Such markers for mammalian cell lines include, for example, the bacterial xanthineguanine phosporibosyl transferase gene, which can be selected for in medium containing mycophenolic acid and xanthine (Mulligan et al. (1981) Proc. Natl. Acad. Sci. USA 78:2072–2076), and the aminoglycoside phosphotransferase gene (specifying a protein that inactivates the antibacterial action of neomycin/kanamycin derivatives), which can be selected for using medium containing neomycin derivatives such as G418 which are normally toxic to mammalian cells (Colbere-Garapin et al. (1981) J. Mol. Biol. 150:1–14). Useful markers for other eucaryotic expression systems, are well known to those of skill in the art.

Infection can be carried out in vitro or in vivo. In vitro infection of cells is performed by adding the gene transfer vectors to the cell culture medium. When infection is carried out in vivo, the solution containing the gene transfer vectors may be administered by a variety of modes, depending on the tissue which is to be infected. Examples of such modes of administration include injection of gene transfer vectors into the skin, topical application onto the skin, direct application to a surface of epithelium, or instillation into an organ (e.g., time release patch or capsule below the skin or into a tumor).

Expression can be amplified by placing an amplifiable gene, such as the mouse dihydrofolate reductase (dhfr) gene adjacent to the coding sequence. Cells can then be selected for methotrexate resistance in dhfr-deficient cells. See, e.g. Urlaub et al. (1980) Proc. Natl. Acad. Sci. USA 77:4216–4220; Rungold et al. (1981) J. Mol. and Appl. Genet. 1:165–175.

The above-described system can be used to direct the expression of a wide variety of procaryotic, eucaryotic and viral proteins, including, for example, viral glycoproteins suitable for use as vaccine antigens, immunomodulators for regulation of the immune response, hormones, cytokines and growth factors, as well as proteins useful in the production of other biopharmaceuticals.

It may also be desirable to produce mutants or analogs of the proteins of interest. Mutants or analogs may be prepared by the deletion of a portion of the sequence encoding the protein, by insertion of a sequence, and/or by substitution of one or more nucleotides within the sequence. Techniques for modifying nucleotide sequences, such as site-directed mutagenesis, are well known to those skilled in the art. See, e.g., Sambrook et al., supra; DNA Cloning, Vols. I and II, supra; Nucleic Acid Hybridization, supra.

It certain embodiments, it may be desirable to further engineer the coding sequence to effect secretion of the polypeptide from the host organism. This enhances clone stability and prevents the toxic build up of proteins in the host cell so that expression can proceed more efficiently. Homologous signal sequences can be used for this purpose with proteins normally found in association with a signal sequence. Additionally, heterologous leader sequences which provide for secretion of the protein can be added to the constructs. Preferably, processing sites will be included such that the leader fragment can be cleaved from the protein expressed therewith. (See, e.g., U.S. Pat. No. 4,336,246 for a discussion of how such cleavage sites can be introduced). The leader sequence fragment typically encodes a signal peptide comprised of hydrophobic amino acids.

In one embodiment of the invention, a heterologous gene sequence, i.e., a therapeutic gene, is inserted into the nucleic acid molecule of the invention. Other embodiments of the isolated nucleic acid molecule of the invention include the addition of a single enhancer element or multiple enhancer elements which amplify the expression of the heterologous therapeutic gene without compromising tissue specificity.

The transformation procedure used depends upon the host to be transformed. Mammalian cells can conveniently be transformed using, for example, DEAE-dextran based procedures, calcium phosphate precipitation (Graham, F. L. and Van der Eb, A. J. (1973) Virology 52:456–467), protoplast fusion, liposome-mediated transfer, polybrene-mediated transfection and direct microinjection of the DNA into nuclei. Bacterial cells will generally be transformed using calcium chloride, either alone or in combination with other divalent cations and DMO (Sambrook, Fritsch & Maniatis, Molecular Cloning: A Laboratory Manual, Second Edition (1989)). DNA can also be introduced into bacterial cells by electroporation. Methods of introducing exogenous DNA into yeast hosts typically include either the transformation of spheroplasts or transformation of intact yeast cells treated with alkali cations.

The constructs can also be used in gene therapy or nucleic acid immunization, to direct the production of the desired gene product in vivo, by administering the expression constructs directly to a subject for the in vivo translation thereof. See, e.g. EPA Publication No. 336,523 (Dreano et al., published Oct. 11, 1989). Alternatively, gene transfer can be accomplished by transfecting the subject's cells or tissues with the expression constructs ex vivo and reintroducing the transformed material into the host. The constructs can be directly introduced into the host organism, i.e., by injection (see International Publication No. WO/90/11092; and Wolff et al., (1990) Science 247:14651468). Liposome-mediated gene transfer can also be accomplished using known methods. See, e.g., Hazinski et al., (1991) Am. J. Respir. Cell Mol. Biol. 4:206–209; Brigham et al. (1989) Am. J. Med. Sci. 298:278–281; Canonico et al. (1991) Clin. Res. 39:219A; and Nabel et al. (1990) Science 249:1285–1288. Targeting agents, such as antibodies directed against surface antigens expressed on specific cell types, can be covalently conjugated to the liposomal surface so that the nucleic acid can be delivered to specific tissues and cells for local administration.

There are several protocols for human gene therapy which have been approved for use by the Recombinant DNA Advisory Committee (RAC) which conform to a general protocol of target cell infection and administration of transfected cells (see for example, Blaese, R. M., et al., 1990; Anderson, W. F., 1992; Culver, K. W. et al., 1991). In addition, U.S. Pat. No. 5,399,346 (Anderson, W. F. et al., Mar. 21, 1995, U.S. Ser. No. 220,175) describes procedures for retroviral gene transfer. The contents of these support references are incorporated in their entirety into the subject application. Retroviral-mediated gene transfer requires target cells which are undergoing cell division in order to achieve stable integration hence, cells are collected from a subject often by removing blood or bone marrow. It may be necessary to select for a particular subpopulation of the originally harvested cells for use in the infection protocol. Then, a retroviral vector containing the gene(s) of interest would be mixed into the culture medium. The vector binds to the surface of the subject's cells, enters the cells and inserts the gene of interest randomly into a chromosome. The gene of interest is now stably integrated and will remain in place and be passed to all of the daughter cells as the cells grow in number. The cells may be expanded in culture for a total of 9–10 days before reinfusion (Culver et al., 1991). As the length of time the target cells are left in culture increases, the possibility of contamination also increases, therefore a shorter protocol would be more beneficial.

This invention provides for the construction of a promoter or a functional equivalent thereof linked to a gene of interest for use in gene therapy or for diagnostic uses. The efficiency of transduction of these vectors can be tested in cell culture systems.

This invention involves targeting a gene-of-interest to the a particular cell so that the protein encoded by the gene is expressed and directly or indirectly ameliorate the diseased state.

After infecting a susceptible cell, the transgene driven by a specific promoter in the vector expresses the protein encoded by the gene. The use of the highly specific gene vector will allow selective expression of the specific genes in cancer cells.

The basic tasks in the present method of the invention are isolating the gene of interest, selecting the proper vector vehicle to deliver the gene of interest to the body, administering the vector having the gene of interest into the body, and achieving appropriate expression of the gene of interest. The present invention provides packaging the cloned genes, i.e. the genes of interest, in such a way that they can be injected directly into the bloodstream or relevant organs of patients who need them. The packaging will protect the foreign DNA from elimination by the immune system and direct it to appropriate tissues or cells.

In one embodiment of the invention, the gene of interest (desired coding sequence) is a bone morphogenetic protein receptor-II gene.

Along with the human or animal gene of interest another gene, e.g., a selectable marker, can be inserted that will allow easy identification of cells that have incorporated the modified retrovirus. The critical focus on the process of gene therapy is that the new gene must be expressed in target cells at an appropriate level with a satisfactory duration of expression.

The methods described herein to modify vectors and administering such modified vectors into the skin are merely for purposes of illustration and are typical of those that might be used. However, other procedures may also be employed, as is understood in the art.

Most of the techniques used to construct vectors and the like are widely practiced in the art, and most practitioners are familiar with the standard resource materials which describe specific conditions and procedures. However, for convenience, the following paragraphs may serve as a guideline.

Construction of suitable vectors containing the desired therapeutic gene coding and control sequences employs standard ligation and restriction techniques, which are well understood in the art (see Maniatis et al., in Molecular Cloning: A Laboratory Manual, Cold Spring Harbor Laboratory, New York (1982)). Isolated plasmids, DNA sequences, or synthesized oligonucleotides are cleaved, tailored, and religated in the form desired.

Site-specific DNA cleavage is performed by treating with the suitable restriction enzyme (or enzymes) under conditions which are generally understood in the art, and the particulars of which are specified by the manufacturer of these commercially available restriction enzymes (See, e.g. New England Biolabs Product Catalog). In general, about 1 $\mu$g of plasmid or DNA sequences is cleaved by one unit of enzyme in about 20 $\mu$l of buffer solution. Typically, an excess of restriction enzyme is used to insure complete digestion of the DNA substrate.

Incubation times of about one hour to two hours at about 37 degree. C. are workable, although variations can be tolerated. After each incubation, protein is removed by extraction with phenol/chloroform, and may be followed by ether extraction, and the nucleic acid recovered from aqueous fractions by precipitation with ethanol. If desired, size separation of the cleaved fragments may be performed by polyacrylamide gel or agarose gel electrophoresis using standard techniques. A general description of size separations is found in Methods in Enzymology 65:499–560 (1980).

Restriction cleaved fragments may be blunt ended by treating with the large fragment of E. coli DNA polymerase I (Klenow) in the presence of the four deoxynucleotide triphosphates (dNTPs) using incubation times of about 15 to 25 min at 20.degree. C. to 25.degree. C. in 50 mM Tris (pH 7.6) 50 mM NaCl, 6 mM $MgCl_2$, 6 mM DTT and 5–10 .mu.M dNTPs. The Klenow fragment fills in at 5' sticky ends but chews back protruding 3' single strands, even though the four dNTPs are present. If desired, selective repair can be performed by supplying only one of the dNTPs, or with selected dNTPs, within the limitations dictated by the nature of the sticky ends. After treatment with Klenow, the mixture is extracted with phenol/chloroform and ethanol precipitated. Treatment under appropriate conditions with S1 nuclease or Bal-31 results in hydrolysis of any single-stranded portion.

Ligations are performed in 10–50 $\mu$l volumes under the following standard conditions and temperatures using T4 DNA ligase. Ligation protocols are standard (D. Goeddel (ed.) Gene Expression Technology: Methods in Enzymology (1991)).

In vector construction employing "vector fragments", the vector fragment is commonly treated with bacterial alkaline phosphatase (BAP) or calf intestinal alkaline phosphatase (CIP) in order to remove the 5' phosphate and prevent religation of the vector. Alternatively, religation can be prevented in vectors which have been double digested by additional restriction enzyme digestion of the unwanted fragments.

Suitable vectors include viral vector systems e.g. ADV, RV, and AAV (R. J. Kaufman "Vectors used for expression in mammalian cells" in Gene Expression Technology, edited by D. V. Goeddel (1991).

Many methods for inserting functional DNA transgenes into cells are known in the art. For example, non-vector methods include nonviral physical transfection of DNA into cells; for example, microinjection (DePamphilis et al., Bio-Technique 6:662–680 (1988)); liposomal mediated transfection (Felgner et al., Proc. Natl. Acad. Sci. USA, 84:7413–7417 (1987), Felgner and Holm, Focus 11:21–25 (1989) and Felgner et al., Proc. West. Pharmacol. Soc. 32: 115–121 (1989)) and other methods known in the art.

One way to get DNA into a target cell is to put it inside a membrane bound sac or vesicle such as a spheroplast or liposome, or by calcium phosphate precipitation ($CaPO_4$) (Graham F. and Van der Eb, A., Virology 52:456 1973; Schaefer-Ridder M., et al., Liposomes as gene carriers: Efficient transduction of mouse L cells by thymidine kinase gene. Science 1982; 215:166; Stavridis J. C., et al., Construction of transferrin-coated liposomes for in vivo transport of exogenous DNA to bone marrow erythroblasts in rabbits. Exp Cell Res 1986; 164:568–572).

A vesicle can be constructed in such a way that its membrane will fuse with the outer membrane of a target cell. The vector of the invention in vesicles can home into the cancer cells.

The spheroplasts are maintained in high ionic strength buffer until they can be fused through the mammalian target cell using fusogens such as polyethylene glycol.

Liposomes are artificial phospholipid vesicles. Vesicles range in size from 0.2 to 4.0 micrometers and can entrap 10% to 40% of an aqueous buffer containing macromolecules. The liposomes protect the DNA from nucleases and facilitate its introduction into target cells. Transfection can also occur through electroporation.

Before administration, the modified vectors may be suspended in complete PBS at a selected density for injection. In addition to PBS, any osmotically balanced solution which is physiologically compatible with the subject may be used to suspend and inject the modified vectors into the host.

For injection, the cell suspension is drawn up into the syringe and administered to anesthetized recipients. Multiple injections may be made using this procedure. The viral suspension procedure thus permits administration of genetically modified vectors to any predetermined site in the skin, is relatively non-traumatic, allows multiple administrations simultaneously in several different sites or the same site using the same viral suspension. Multiple injections may consist of a mixture of therapeutic genes.

Expression of a gene is controlled at the transcription, translation or post-translation levels. Transcription initiation is an early and critical event in gene expression. This depends on the promoter and enhancer sequences and is influenced by specific cellular factors that interact with these sequences. The transcriptional unit of many prokaryotic genes consists of the promoter and in some cases enhancer or regulator elements (Banerji et al., Cell 27:299 (1981); Corden et al., Science 209:1406 (1980); and Breathnach and Chambon, Ann. Rev. Biochem. 50:349 (1981)).

For retroviruses, control elements involved in the replication of the retroviral genome reside in the long terminal repeat (LTR) (Weiss et al., eds., In: The molecular biology of tumor viruses: RNA tumor viruses, Cold Spring Harbor Laboratory, Cold Spring Harbor, N.Y. (1982)).

Moloney murine leukemia virus (MLV) and Rous sarcoma virus (RSV) LTRs contain promoter and enhancer sequences (Jolly et al., Nucleic Acids Res. 11:1855 (1983); Capecchi et al., In: Enhancer and eukaryotic gene expression, Gulzman and Shenk, eds., pp. 101–102, Cold Spring Harbor Laboratories, Cold Spring Harbor, N.Y.).

Promoter and enhancer regions of a number of non-viral promoters have also been described (Schmidt et al., Nature 314:285 (1985); Rossi and de Crombrugghe, Proc. Natl. Acad. Sci. USA 84:5590–5594 (1987)).

In addition to using viral and non-viral promoters to drive therapeutic gene expression, an enhancer sequence may be used to increase the level of therapeutic gene expression. Enhancers can increase the transcriptional activity not only of their native gene but also of some foreign genes (Armelor, Proc. Natl. Acad. Sci. USA 70:2702 (1973)).

Therapeutic gene expression may also be increased for long term stable expression after injection using cytokines to modulate promoter activity.

The methods of the invention are exemplified by preferred embodiments in which modified vectors carrying a therapeutic gene are injected intracerebrally into a subject.

The most effective mode of administration and dosage regimen for the molecules of the present invention depends upon the exact location of the disease being treated, the severity and course of the disease, the subject's health and response to treatment and the judgment of the treating physician. Accordingly, the dosages of the molecules should be titrated to the individual subject. The molecules may be delivered directly or indirectly via another cell, autologous cells are preferred, but heterologous cells are encompassed within the scope of the invention.

The interrelationship of dosages for animals of various sizes and species and humans based on mg/m.sup.2 of surface area is described by Freireich, E. J., et al. Cancer Chemother., Rep. 50 (4):219–244 (1966). Adjustments in the dosage regimen may be optimized, e.g., doses may be divided and administered on a daily basis or the dose reduced proportionally depending upon the situation (e.g., several divided dose may be administered daily or proportionally reduced depending on the specific therapeutic situation).

It would be clear that the dose of the molecules of the invention required to achieve cures may be further reduced with schedule optimization.

Liposomes could be used as a delivery agent to introduce the nucleic acid construct to the cells of the subject to be treated. Of course, there are many ways to deliver such a nucleic acid construct which would be known to one of skill in the art (e.g. microinjection; topical application; use of a chemical vehicle; direct injection into the tumor; etc.).

This invention provides a method of preventing and/or treating Familial Primary Pulmonary Hypertension in a subject which comprises administering to the subject an amount of wildtype bone morphogenetic protein receptor-II effective to prevent and/or treat Familial Primary Pulmonary Hypertension so as to thereby prevent and/or treat Familial Primary Pulmonary Hypertension in the subject. This invention provides a method of preventing and/or treating Familial Primary Pulmonary Hypertension in a subject which comprises administering to the subject an effective amount of a wildtype bone morphogenetic protein receptor-II polypeptide comprising consecutive amino acids having the sequence set forth in SEQ ID NO:2 to prevent and/or treat Familial Primary Pulmonary Hypertension in the subject.

As used herein, "administering" may be effected or performed using any of the methods known to one skilled in the art. The compound may be administered by various routes including but not limited to aerosol, intravenous, oral or topical route. The administration may comprise intralesional, intraperitoneal, subcutaneous, intramuscular or intravenous injection; infusion; liposome-mediated delivery; topical, intrathecal, gingival pocket, per rectum, intrabronchial, nasal, transmucosal, intestinal, oral, ocular or otic delivery. In a further embodiment, the administration includes intrabronchial administration, anal, intrathecal administration or transdermal delivery. The compounds and/or agents of the subject invention may be delivered locally via a capsule which allows sustained release of the agent or the peptide over a period of time. Controlled or sustained release compositions include formulation in lipophilic depots (e.g., fatty acids, waxes, oils). Also comprehended by the invention are particulate compositions coated with polymers (e.g., poloxamers or poloxamines) and the agent coupled to antibodies directed against tissue-specific receptors, ligands or antigens or coupled to ligands of tissue-specific receptors. Other embodiments of the compositions of the invention incorporate particulate forms protective coatings, protease inhibitors or permeation enhancers for various routes of administration, including parenteral, pulmonary, nasal and oral. The carrier includes but is not limited to those which are a diluent, an aerosol, a topical carrier, an aqueous solution, a nonaqueous solution or a solid carrier.

This invention provides a method of detecting whether a subject is either predisposed to or afflicted with Familial Primary Pulmonary Hypertension which comprises:

a) obtaining a suitable nucleic acid sample from the subject; and b) detecting the presence of a $(GGC)_{12}$ trinucleotide repeat at positions −928 to −963 in the 5' end of the bone morphogenetic protein receptor-II gene, wherein the presence of the trinucleotide repeat indicates that the subject is either predisposed to or afflicted with Familial Primary Pulmonary Hypertension.

This invention provides a method of screening for a compound capable of treating Familial Primary Pulmonary Hypertension which comprises:

a) contacting a cell which expresses a mutant bone morphogenetic protein receptor-II with the compound; and b) determining whether the compound is capable of reversing the functional deficit in Familial Primary Pulmonary Hypertension, wherein a reversal of the functional deficit indicates that the compound is capable of treating Familial Primary Pulmonary Hypertension. In one embodiment of the subject invention, the functional deficit is reduced kinase activity for the bone morphogenetic protein receptor-II.

This invention provides a method of obtaining a composition which comprises:

a) identifying a compound capable of treating Familial Primary Pulmonary Hypertension by the above method; and
b) admixing the compound so identified or a homolog or derivative thereof with a carrier.

In one embodiment, the compound is recovered before being admixed with a carrier.

The carriers include but are not limited to an aerosol, intravenous, oral and topical carriers. Accordingly, the invention provides the above composition adapted for aerosol, intravenous, oral or topical applications or other applications known to one skilled in the art.

This invention provides the agents, compounds and/or compositions described herein and carrier. Such carrier may be a pharmaceutically acceptable carrier. Pharmaceutically acceptable carriers are well known to those skilled in the art. Such pharmaceutically acceptable carriers may include but are not limited to aqueous or non-aqueous solutions, suspensions, and emulsions. Examples of non-aqueous solvents are propylene glycol, polyethylene glycol, vegetable oils such as olive oil, and injectable organic esters such as ethyl oleate. Aqueous carriers include water, alcoholic/aqueous solutions, emulsions or suspensions, saline and buffered media. Parenteral vehicles include sodium chloride solution, Ringer's dextrose, dextrose and sodium chloride, lactated Ringer's or fixed oils. Intravenous vehicles include fluid and nutrient replenishers, electrolyte replenishers such as those based on Ringer's dextrose, and the like. Preservatives and other additives may also be present, such as, for example, antimicrobials, antioxidants, chelating agents, inert gases and the like.

As used herein, "composition" means a mixture. The compositions include but are not limited to those suitable for oral, rectal, intravaginal, topical, nasal, opthalmic, or parenteral administration to a subject. As used herein, "parenteral" includes but is not limited to subcutaneous, intravenous, intramuscular, or intrasternal injections or infusion techniques. As used herein, "administering" may be effected or performed using any of the methods known to one skilled in the art. The methods for administration to the subject include but are not limited to oral, rectal, intravaginal, topical, nasal, opthalmic, parenteral subcutaneous, intravenous, intramuscular, or intrasternal injections or infusion techniques.

This invention provides a transgenic non-human animal whose cells comprise a mutant nucleic acid which encodes a bone morphogenetic protein receptor-II polypeptide. In one embodiment, the non-human animal exhibits primary pulmonary hypertension. In one embodiment, the nucleic acid is operatively linked to a promotor. In one embodiment, the non-human animal is a mouse, a rat, a sheep, a dog, a primate or a reptile. This invention provides a transgenic mouse which comprises a mutation in a gene which encodes a bone morphogenetic protein receptor-II. In one embodiment, the transgenic animal is a mouse.

Transgenics

The following U.S. Patents are hereby incorporated by reference: U.S. Pat. No. 6,025,539, IL-5 transgenic mouse; U.S. Pat. No. 6,023,010, Transgenic non-human animals depleted in a mature lymphocytic cell-type; U.S. Pat. No. 6,018,098, In vivo and in vitro model of cutaneous photoaging; U.S. Pat. No. 6,018,097, Transgenic mice expressing human insulin; U.S. Pat. No. 6,008,434, Growth differentiation factor-11 transgenic mice; U.S. Patent No. 6,002,066; H2-M modified transgenic mice; U.S. Pat. No. 5,994,618, Growth differentiation factor-8 transgenic mice; U.S. Pat. No. 5,986,171, Method for examining neurovirulence of polio virus, U.S. Pat. No. 5,981,830, Knockout mice and their progeny with a disrupted hepsin gene; U.S. Pat. No. 5,981,829, .DELTA.Nur77 transgenic mouse; U.S. Pat. No. 5,936,138; Gene encoding mutant L3T4 protein which facilitates HIV infection and transgenic mouse expressing such protein; U.S. Pat. No. 5,912,411, Mice transgenic for a tetracycline-inducible transcriptional activator; U.S. Pat. No. 5,894,078, Transgenic mouse expressing C-100 app.

The methods used for generating transgenic animals, including but not limited to mice are well known to one of skill in the art. For example, one may use the manual entitled "Manipulating the Mouse Embryo" by Brigid Hogan et al. (Ed. Cold Spring Harbor Laboratory) 1986.

See for example, Leder and Stewart, U.S. Pat. No. 4,736,866 for methods for the production of a transgenic mouse.

For sometime it has been known that it is possible to carry out the genetic transformation of a zygote (and the embryo and mature organism which result therefrom) by the placing or insertion of exogenous genetic material into the nucleus of the zygote or to any nucleic genetic material which ultimately forms a part of the nucleus of the zygote. The genotype of the zygote and the organism which results from a zygote will include the genotype of the exogenous genetic material. Additionally, the inclusion of exogenous genetic material in the zygote will result in a phenotype expression of the exogenous genetic material.

The genotype of the exogenous genetic material is expressed upon the cellular division of the zygote. However, the phenotype expression, e.g., the production of a protein product or products of the exogenous genetic material, or alterations of the zygote's or organism's natural phenotype, will occur at that point of the zygote's or organism's development during which the particular exogenous genetic material is active. Alterations of the expression of the phenotype include an enhancement or diminution in the expression of a phenotype or an alteration in the promotion and/or control of a phenotype, including the addition of a new promoter and/or controller or supplementation of an existing promoter and/or controller of the phenotype.

The genetic transformation of various types of organisms is disclosed and described in detail in U.S. Pat. No. 4,873,191, issued Oct. 10, 1989, which is incorporated herein by reference to disclose methods of producing transgenic organisms. The genetic transformation of organisms can be used as an in vivo analysis of gene expression during differentiation and in the elimination or diminution of genetic diseases by either gene therapy or by using a transgenic non-human mammal as a model system of a human disease. This model system can be used to test putative drugs for their potential therapeutic value in humans.

The exogenous genetic material can be placed in the nucleus of a mature egg. It is preferred that the egg be in a fertilized or activated (by parthenogenesis) state. After the addition of the exogenous genetic material, a complementary haploid set of chromosomes (e.g., a sperm cell or polar body) is added to enable the formation of a zygote. The zygote is allowed to develop into an organism such as by implanting it in a pseudopregnant female. The resulting organism is analyzed for the integration of the exogenous genetic material. If positive integration is determined, the organism can be used for the in vivo analysis of the gene expression, which expression is believed to be related to a particular genetic disease.

The "transgenic non-human animals" of the invention are produced by introducing "transgenes" into the germline of the non-human animal. Embryonal target cells at various developmental stages can be used to introduce transgenes. Different methods are used depending on the stage of development of the embryonal target cell. The zygote is the best target for micro-injection. In the mouse, the male pronucleus reaches the size of approximately 20 micrometers in diameter which allows reproducible injection of 1–2 pl of DNA solution. The use of zygotes as a target for gene transfer has a major advantage in that in most cases the injected DNA will be incorporated into the host gene before the first cleavage (Brinster, et al. (1985) Proc. Natl. Acad. Sci. U.S.A. 82, 4438–4442). As a consequence, all cells of the transgenic non-human animal will carry the incorporated transgene. This will in general also be reflected in the efficient transmission of the transgene to offspring of the founder since 50% of the germ cells will harbor the transgene. Microinjection of zygotes is the preferred method for incorporating transgenes in practicing the invention.

Retroviral infection can also be used to introduce transgene into a non-human animal. The developing non-human embryo can be cultured in vitro to the blastocyst stage. During this time, the blastomeres can be targets for retroviral infection (Jaenich, R. (1976) Proc. Natl. Acad. Sci U.S.A. 73, 1260–1264). Efficient infection of the blastomeres is obtained by enzymatic treatment to remove the zona pellucida (Hogan, et al. (1986) in Manipulating the Mouse Embryo, Cold Spring Harbor Laboratory Press, Cold Spring Harbor, N.Y.).

The viral vector system used to introduce the transgene is typically a replication-defective retrovirus carrying the transgene (Jahner, et al. (1985) Proc. Natl. Acad. Sci. U.S.A. 82, 6927–6931; Van der Putten, et al. (1985) Proc. Natl. Acad. Sci U.S.A. 82, 6148–6152). Transfection is easily and efficiently obtained by culturing the blastomeres on a monolayer of virus-producing cells (Van der Putten, supra; Stewart, et al. (1987) EMBO J. 6, 383–388). Alternatively, infection can be performed at a later stage. Virus or virus-producing cells can be injected into the blastocoele (Jahner, D., et al. (1982) Nature 298, 623–628). Most of the founders will be mosaic for the transgene since incorporation occurs only in a subset of the cells which formed the transgenic non-human animal. Further, the founder may contain various retroviral insertions of the transgene at different positions in the genome which generally will segregate in the offspring. In addition, it is also possible to introduce transgenes into the germ line, albeit with low efficiency, by intrauterine retroviral infection of the midgestation embryo (Jahner, D. et al. (1982) supra).

A third type of target cell for transgene introduction is the embryonal stem cell (ES). ES cells are obtained from pre-implantation embryos cultured in vitro and fused with embryos (Evans, M. J., et al. (1981) Nature 292, 154–156; Bradley, M. O., et al. (1984) Nature 309, 255–258; Gossler, et al. (1986) Proc. Natl. Acad. Sci U.S.A. 83, 9065–9069; and Robertson, et al. (1986) Nature 322, 445–448). Transgenes can be efficiently introduced into the ES cells by DNA transfection or by retrovirus-mediated transduction. Such transformed ES cells can thereafter be combined with blastocysts from a non-human animal. The ES cells thereafter colonize the embryo and contribute to the germ line of the resulting chimeric animal. For review see Jaenisch, R. (1988) Science 240, 1468–1474.

As used herein, a "transgene" is a DNA sequence introduced into the germline of a non-human animal by way of human intervention such as by way of the above described methods.

Asthma:

We have previously observed an individual who had been mis-diagnosed with asthma, but actually had PPH (Morse and Barst, 1997). This was possible due to the strong suspicion of PPH because of a family history of the disease. Now that the gene for PPH at PPH1 has been identified it is possible to screen for mutations in BMPR2 in all patients who present with the symptoms of asthma to prevent mis-diagnosis and mis-treatment of PPH as asthma. Symptoms of asthma include but are not limited to wheezing and intermittent shortness of breath. Screening panels of many genes that are risk factors for asthma are available to aid physicians in making the diagnosis. The PPH1 gene (BMPR2) may be included in such panels to rule out PPH, a disease that can present with the symptoms of asthma. This is analogous to the present day practice of screening all persons who present with a first-break psychotic disorder for Wilson's disease, even though most of them will have schizophrenia and bipolar disorder.

Twinning:

We have observed an increased rate of twinning in our collection of families. Identification of BMPR2 as PPH1 sheds light on why this may occur. It has recently been observed that sheep that have only one functional copy of the ligand BMP15 (bone morphogenetic protein 15) have an increased rate of twin and triplet births (Galloway et al., 2000). BMPR2 is a receptor for BMP15 and hence having only one functional copy of the receptor in the families with PPH is directly analogous to having only one functional copy of the ligand, and is likely to be responsible for the increased rate of twinning observed. Accordingly, subject of the subject invention may be a female subject, i.e. the mother, or a male subject, i.e. the father.

In Vitro Methods for Drug Screening:

Identification of BMPR2 as PPH1 enables the design and use of in vitro methods of screening for compounds that might correct the functional deficit in the disorder. One functional deficit is reduced amount or a lack of kinase activity. Cell lines are constructed that express forms of mutant BMPR2 as described herein, and the rest of the BMP signaling pathway. The function of this pathway is then assayed in vitro, with and without exogenous compounds and those that return function to normal are considered as candidates as therapeutic agents for treatment of the disorder.

Pharmacogenetics:

Knowledge of BMPR2 as PPH1 enables testing of outcome and side effects to therapeutic agents on the basis of disease mutations for PPH and common polymorphisms in the BMPR2 gene and other genes of the BMP signaling pathway.

Mouse Models for Drug Screening:

Knowledge of BMPR2 as PPH1 enables the construction of inbred mouse strains containing the exact mutations described in this application in the highly homologous mouse gene, or after disabling the mouse gene, a copy of the human gene inserted into the mouse. These inbred strains are then useful as reagents for in vivo tests of compounds that act as therapeutic agents for treatment of PPH.

According to one aspect, the present invention is directed to a peptide or polypeptide encoded by the mutant BMPR2 nucleic acid sequences of the invention or a fragment thereof. Another embodiment of the present invention is a purified or isolated nucleotide sequence encoding the above identified mutant BMPR2 nucleic acid sequences of the invention and fragments thereof. Another embodiment is a purified or isolated nucleotide sequence which hybridizes to the polynucleotide sequence encoding the above-mentioned mutant BMPR2 nucleic acid sequences of the invention and fragments thereof. One skilled in the art would be able to determine the preferred hybridization conditions.

Another embodiment is a host cell transformed with a polynucleotide sequence encoding the above-mentioned mutant BMPR2 peptide or polypeptide sequences of the invention and fragments.

Transformation of a host cell with recombinant DNA may be carried out by conventional techniques known in the art. Where the host is prokaryotic, such as *E. coli*, competent cells which are capable of DNA uptake can be prepared from cells harvested after the exponential growth phase and subsequently treated by the CaCl2 method by procedures well known in the art. Alternatively, MgC12 or RbCl can be used. Transformation can also be performed after forming a protoplast of the host cell or by electroporation.

When the host is eukaryote, such methods of transfection of DNA as calcium phosphate co-precipitates, conventional mechanical procedures such as micro-injection, electroporation, insertion of a plasmid encased in liposomes, or virus vectors may be used. Eukaryotic cells can also be cotransformed with DNA sequences encoding the mutant BMPR2 polypeptide sequences of the invention, and a second foreign DNA molecule encoding a selectable phenotype, such as the herpes simplex thymidine kinase gene. Another method is to use a eukaryotic viral vector, such as simian virus 40 (SV40) or bovine papilloma virus, to transiently infect or transform eukaryotic cells and express the protein. EUKARYOTIC VIRAL VECTORS Gluzman (ed.), Cold Spring Harbor Laboratory, 1982.

Isolation and purification of the mutant BMPR2 peptide or polypeptide sequences of the invention expressed by a transformed host may be carried out by conventional means including preparative chromatography and immunological separations involving monoclonal or polyclonal antibodies.

Antibodies provided in the present invention are immunoreactive with the mutant BMPR2 peptides and polypeptides.

Another embodiment is a recombinant expression vector containing the above-mentioned nucleotide sequences. Preferably, the vector is a virus. Preferred viruses are RNA viruses and preferred RNA viruses are retroviruses. Another preferred vector is a liposome, preferably a target-specific liposome which may be targeted with, for example, an antibody or ligand. Another preferred vector is a plasmid.

Another embodiment is an antibody which binds to the above-mentioned peptides. The antibody may be polyclonal or monoclonal. Using the isolated peptides, antibodies are prepared which are capable of determining the presence or absence of peptide products encoded by the pulmonary hypertension-linked nucleotide sequences. One embodiment of the present invention is directed to these antibodies. Furthermore, another embodiment of the present invention is directed to antibodies which can detect individuals at risk of developing pulmonary hypertension (even in individuals who have not clinically manifested any symptoms of the disease).

Another embodiment is a method for detecting the risk of developing or for diagnosing pulmonary hypertension, preferably primary pulmonary hypertension, comprising contacting a cellular component from the subject with an antibody or nucleic acid probe which binds to a cellular component associated with the pulmonary hypertension. In one embodiment, the cellular component is taken from the subject's lung tissue and is a nucleic acid. Preferably, the nucleic acid is DNA encoding the above-mentioned disease-linked peptides or fragments. Also preferred as a nucleic acid is RNA. Another preferred cellular component is the above-mentioned peptides and fragments.

Preferably, the nucleic acid probe specifically hybridizes to the above-mentioned cellular component. When the reagent is a nucleic acid probe, it is preferably detectably labeled. Preferred labels include a radioisotope, a bioluminescent compound, a chemiluminescent compound, a fluorescent compound, a metal chelate, and an enzyme.

Alternatively, if the cellular component is a peptide or fragment, then an antibody is used which specifically binds to the peptide or fragment. As noted above, the antibody may be monoclonal or polyclonal.

Another embodiment is a method of gene therapy, comprising introducing into the cells of a host subject an expression vector comprising a polynucleotide sequence encoding the non-mutant, "normal" BMPR2 sequence. Preferably, the expression vector is introduced into the cells of the host subject ex vivo, yielding transformed cells, and the transformed cells then are reintroduced into the subject. A preferred expression vector for this purpose is an RNA virus, preferably a retrovirus.

Another embodiment is a kit for detecting pulmonary hypertension comprising a nucleic acid probe that binds to a polynucleotide sequence encoding one of the above-mentioned peptides or fragments. Preferably, the probe is labeled for ease of detection with a label as described above. Alternatively, the kit may comprise an antibody which specifically binds to one of the above-mentioned peptides or fragments. Still another alternative is to use an oligonucleotide primer in the kit that permits amplification of a target polynucleotide sequence encoding one of the above-mentioned peptides or fragments, for example, by polymerase chain reaction (PCR) amplification.

Peptides of the invention can be synthesized by the well known solid phase peptide synthesis methods described, for example, by Merrifield, J. Am. Chem. Soc. 85: 2149 (1962), and by Stewart and Young, SOLID PHASE PEPTIDES SYNTHESIS 27–62 (Freeman Publ., 1969).

The polyclonal and monoclonal antibodies of the invention are immunoreactive with the peptides or immunogenic fragments of the peptides. If desired, polyclonal antibodies can be further purified, for example, by binding to and elution from a matrix to which peptide is bound or by utilizing common peptides to selectively remove non-specific antibodies. Antibody which consists essentially of pooled monoclonal antibodies with different epitopic specificities, as well as distinct mono-clonal antibody preparations are provided. The term "antibody" as used in this invention includes intact molecules as well as fragments thereof, such as Fab and F(ab')2 fragments, and chimeric, human and humanized antibodies, which are functionally capable of binding an epitopic determinant of the peptides.

A preferred method for the identification and isolation of antibody binding domains which exhibit binding with the peptides is the bacteriophage 1 vector system. This vector system has been used to express a combina-torial library of Fab fragments from the mouse antibody repertoire in *Escherichia coli*, see Huse et al., Science 246: 1275–81 (1989), and from the human antibody repertoire. Mullinax et al., Proc. Nat'l Acad. Sci. USA 87: 8095–99 (1990).

For purposes of the invention, an antibody or nucleic acid probe specific for the peptide may be used to detect the presence of the peptide (in the case of an antibody probe) or nucleotide (in the case of the nucleic acid probe) in biological fluids or tissues suspected of containing the peptide. Oligonucleotide primers based on any coding sequence region in the peptide sequence are useful for amplifying DNA or RNA, for example by PCR. Any specimen containing a detectable amount of antigen can be used. A preferred sample of this invention is tissue taken from the lung. Alternatively, biological fluids which may contain cells of the lung may be used.

The term "subject" as used herein includes but is not limited to mammals. In a preferred embodiment, the subject is a human being.

Another technique which may also result in greater sensitivity consists of coupling the probe to low molecular weight haptens. These haptens can then be specifically detected by means of a second reaction. For example, it is common to use such haptens as biotin, which reacts with avidin, or dinitrophenol, pyridoxal, and fluorescein, which can react with specific antihapten antibodies.

The monoclonal antibodies of the invention are suitable for use in immunoassays in which they can be utilized in liquid phase or bound to a solid phase carrier. In addition, the monoclonal antibodies in these immunoassays can be detectably labeled in various ways. Examples of types of immunoassays which can utilize monoclonal antibodies of the invention are competitive and non-competitive immunoassays in either a direct or indirect format. Examples of such immunoassays are the radioimmunoassay (RIA) and the sandwich (immuno-metric) assay. Detection of the antigens using the monoclonal antibodies of the invention can be performed utilizing immunoassays which are run in either the forward, reverse, or simultaneous modes, including immunohistochemical assays on physiological samples. Alternatively, the antibody of the invention can be used to detect peptides present in electrophoretically dispersed gel protocols such as Western blots and two-dimensional gels.

The monoclonal antibodies of the invention can be bound to many different carriers and used to detect the presence of a peptide of the invention. Examples of well-known carriers include glass, polystyrene, polypropylene, polyethylene, dextran, nylon, amylases, natural and modified celluloses, poly-acryl-amides, agaroses and magnetite. The nature of the carrier can be either soluble or insoluble for purposes of the invention.

In performing the assays it may be desirable to include certain "blockers" in the incubation medium (usually added with the labeled soluble antibody). The "blockers" are added to assure that non-specific proteins, proteases, or anti-heterophilic immunoglobulins to anti-peptide immunoglobulins present in the experimental sample do not cross-link or destroy the antibodies on the solid phase support, or the radiolabeled indicator anti-body, to yield false positive or false negative results. The selection of "blockers" therefore may add substantially to the specificity of the assays described in the present invention.

It has been found that a number of nonrelevant (i.e., nonspecific) antibodies of the same class or subclass (isotype) as those used in the assays (e.g., IgGl, IgG2a, IgM, etc.) can be used as "blockers." The "blockers" are used at a level high enough to maintain the proper sensitivity yet inhibit any unwanted interference by mutually occurring cross reactive proteins in the specimen (normally 1–100 mg/ml).

In this description, the term "epitope" denotes any determinant capable of specific interaction with the monoclonal antibodies of the invention. Epitopic determinants usually comprise chemically active surface groupings of molecules such as amino acids or sugar side chains and usually have specific three dimensional structural characteristics, as well as specific charge characteristics.

In using the monoclonal antibodies of the invention for the in vivo detection of antigen, the detectably labeled monoclonal antibody is given in a dose which is diagnostically effective. The term "diagnostically effective" means that the amount of delectably labeled monoclonal antibody is administered in sufficient quantity to enable detection of the site having the antigen for which the monoclonal antibody is specific. The dosage of detectably labeled monoclonal antibody for in vivo diagnosis will vary depending on such factors as age, sex, and extent of disease of the individual. The dosage of monoclonal antibody can vary from about 0.001 mg/m2, to about 500 mg/m2, preferably 0.1 mg/m2 to about 200 mg/m2, most preferably about 0.1 mg/m2 to about 10 mg/m2. Such dosages may vary, for example, depending on whether multiple injections are given and other factors.

For in vivo diagnostic imaging, the type of detection instrument available is a major factor in selecting a given radioisotope. The radioisotope chosen must have a type of decay which is detectable for a given type of instrument. Still another important factor in selecting a radioisotope for in vivo diagnosis is that the half-life of the radioisotope be long enough so that it is still detectable at the time of maximum uptake by the target, but short enough so that deleterious radiation with respect to the host is minimized. Ideally, a radioisotope used for in vivo imaging will lack a particle emission, but produce a large number of photons in the 140–250 keV range, which may be readily detected by conventional gamma cameras.

For in vivo diagnosis, radioisotopes may be bound to immunoglobulin either directly or indirectly by using an intermediate functional group. Intermediate functional groups which often are used to bind radioisotopes which exist as metallic ions to immunoglobulins are the bifunctional chelating agents such as diethylene-triamine-pentacetic acid (DTPA) and ethylenediaminetetraacetic acid (EDTA) and similar molecules. Typical examples of metallic ions which can be bound to the monoclonal anti-bodies of the invention are 111In, 97Ru, 67Ga, 68Ga, 72As, 89Zr, and 201Tl.

The monoclonal antibodies of the invention can also be labeled with a paramagnetic isotope for purposes of in vivo diagnosis, as in magnetic resonance imaging (MRI) or electron spin resonance (ESR). In general, any conventional method for visualizing diagnostic imaging can be utilized. Usually gamma and positron emitting radioisotopes are used for camera imaging and para-magnetic isotopes for MRI. Elements which are particularly useful in such techniques include 157Gd, 55Mn, 162Dy, 52Cr, and 56Fe.

The monoclonal antibodies of the invention can be used to monitor the course of amelioration of pulmonary hypertension. Thus, by measuring the increase or decrease in the number of cells expressing a peptide or changes in peptide present in various body fluids, such as samples of lung tissue or material wiped or swabbed from lung tissue, it would be possible to determine whether a particular therapeutic regimen aimed at ameliorating the disorder is effective.

The monoclonal antibodies of the invention can also be used, alone or in combination with effector cells, see Douillard et al., Hybridoma 5 (Supp. 1): S139 (1986), for treatment of pulmonary hypertension in a subject.

When used for immunotherapy, the monoclonal antibodies of the invention may be unlabeled or attached to a therapeutic agent. These agents can be coupled either directly or indirectly to the monoclonal antibodies of the invention. One example of indirect coupling is by use of a spacer moiety. These spacer moieties, in turn, can be either insoluble or soluble, see Diener et al., Science 231: 148 (1986), and can be selected to enable drug release from the monoclonal antibody molecule at the target site. Examples of therapeutic agents which can be coupled to the monoclonal antibodies of the invention for immunotherapy are drugs, radioisotopes, lectins, and toxins.

The drugs which can be conjugated to the monoclonal antibodies of the invention include non-proteinaceous as well as proteinaceous drugs. The terms "non-proteinaceous drugs" encompasses compounds which are classically referred to as drugs, for example, mitomycin C, daunorubicin, vinblastine, and others used to treat cancer.

The proteinaceous drugs with which the monoclonal antibodies of the invention can be joined include immunomodulators and other biological response modifiers. The term "biological response modifiers" encompasses substances which are involved in modifying the biological response in such manner as to ameliorate or eliminate pulmonary hypertension. Examples of immune response modifiers include such compounds as flolan, beraprost, and uniprost.

It is also possible to utilize liposomes with the monoclonal antibodies of the invention in their membrane to specifically deliver the liposome to the tissue expressing the mutant peptide. These liposomes can be produced such that they contain, in addition to the monoclonal antibody, such immunotherapeutic agents as those described above which would then be released at the tumor site. Wolff et al., Biochemical et Biophysical Acta 802: 259 (1984).

The dosage ranges for the administration of monoclonal antibodies of the invention are those large enough to produce the desired effect in which the symptoms of the disease are ameliorated. The dosage should not be so large as to cause adverse side effects, such as unwanted cross-reactions, anaphylactic reactions, and the like. Generally, the dosage will vary with the age, condition, sex and extent of the disease in the patient and can be determined by one of skill in the art. The dosage can be adjusted by the individual physician in the event of any complication. Dosage can vary from about 0.1 mg/kg to about 2000 mg/kg, preferably about 0.1 mg/kg to about 500 mg/kg, in one or more dose administrations daily, for one or several days. Generally, when the monoclonal antibodies of the invention are administered conjugated with therapeutic agents, lower dosages, comparable to those used for in vivo diagnostic imaging, can be used.

The monoclonal antibodies of the invention can be administered parenterally by injection or by gradual perfusion over time. The monoclonal antibodies of the invention can be administered intravenously, intra-peritoneally, intramuscularly, subcutaneously, intra-cavity, or transdermally, alone or in combination with effector cells.

The present invention also provides a method for treating a subject with pulmonary hypertension using a nucleotide sequence encoding the non-mutant peptide.

Ribozymes are RNA molecules possessing the ability to specifically cleave other single-stranded RNA in a manner analogous to DNA restriction endonucleases. Through the modification of nucleotide sequences which encode these RNAs, it is possible to engineer molecules that recognize specific nucleotide sequences in an RNA molecule and cleave it. Cech, J. Amer. Med. Assn. 260: 3030 (1988). A major advantage of this approach is that, because they are sequence-specific, only mRNAs with particular sequences are inactivated.

There are two basic types of ribozymes namely, tetrahymena-type (Hasselhoff, Nature, 334:585, 1988) and "hammerhead"-type. Tetrahymena-type ribozymes recognize sequences which are four bases in length, while "hammerhead"-type ribozymes recognize base sequences 11–18 bases in length. The longer the recognition sequence, the greater the likelihood that sequence will occur exclusively in the target mRNA species. Consequently, hammerhead-type ribozymes are preferable to tetrahymena-type ribozymes for inactivating a specific mRNA species and 18-based recognition sequences are preferable to shorter recognition sequences.

The present invention also provides gene therapy for the treatment of pulmonary hypertension mediated by the mutant sequences described herein. Such therapy requires introduction of the appropriate, normal nucleotide sequence (antisense or encoding strand) into cells of subjects having the proliferative disorder. Such therapy may utilize ex vivo transformation of cells followed by their re-introduction into a subject or direct administration of the normal peptide or nucleotide sequence encoding it. Various viral vectors which can be utilized for gene therapy as taught herein include adenovirus, herpes virus, vaccinia, or, preferably, an RNA virus such as a retrovirus. Preferably, the retroviral vector is a derivative of a murine or avian retrovirus. Examples of retroviral vectors in which a single foreign gene can be inserted include, but are not limited to: Moloney murine leukemia virus (MoMuLV), Harvey murine sarcoma virus (HaMuSV), murine mammary tumor virus (MUMTV), and Rous Sarcoma Virus (RSV). A number of additional retroviral vectors can incorporate multiple genes. All of these vectors can transfer or incorporate a gene for a selectable marker so that transduced cells can be identified and generated. By inserting a sequence of interest into the viral vector along with another gene which encodes the ligand for a receptor on a specific target cell, for example, the vector is rendered target specific. Retroviral vectors can be made target specific by inserting, for example, a polynucleotide encoding a sugar, a glycolipid, or a protein. Preferred targeting is accomplished by using an antibody to target the retroviral vector.

Since recombinant retroviruses are defective in one or more genes, they require assistance in order to produce infectious vector particles. Helper cell lines which have deletions of the packaging signal include but are not limited to Y2, PA317 and PA12, for example. These cell lines produce empty virions, since no genome is packaged. If a retroviral vector is introduced into such cells in which the packaging signal is intact, but the structural genes are replaced by other genes of interest, the vector can be packaged and vector virion produced.

Alternatively, NIH 3T3 or other tissue culture cells can be directly transfected with plasmids encoding the retroviral structural genes gag, pl and env by conventional calcium phosphate transfection. These cells are then transfected with the vector plasmid containing the genes of interest. The resulting cells release the retroviral vector into the culture medium.

Other targeted delivery systems for nucleotides include macromolecule complexes, nanocapsules, microspheres, beads, and lipid-based systems including oil-in-water emulsions, micelles, mixed micelles, and liposomes. Liposomes are artificial membrane vesicles which are useful as delivery vehicles in vitro and in vivo. It has been shown that large unilamellar vesicles (ULV), which range in size from 0.2–4.0 $\mu$m can encapsulate a substantial percentage of an aqueous buffer containing large macromolecules. RNA, DNA and intact virions can be encapsulated within the aqueous interior and be delivered to cells in a biologically active form. Fraley et al., Trends Biochem. Sci. 6: 77 (1981).

The composition of the liposome is usually a combination of phospholipids particularly high-phase-transition-temperature phospholipids, usually in combination with steroids, especially cholesterol. Other phospholipids or other lipids may also be used. The physical characteristics of liposomes depend on pH, ionic strength, and the presence of divalent cations.

Examples of lipids useful in liposome production include phosphatidyl compounds, such as phosphati-dyl-glycerol, phosphatidylcholine, phosphatidyiserine, phosphatidylethanolamine, sphingolipids, cerebrosides, and gangliosides. Particularly useful are diacyl-phosphatidylglycerols, where the lipid moiety contains from 14–18 carbon atoms, particularly from 16–18 carbon atoms, and is saturated. Illustrative phospholipids include egg phosphatidylcholine, dipalmitoyl-phosphati-dylcholine and distearoylphosphatidylcholine.

The targeting of liposomes has been classified based on anatomical and mechanistic factors. Anatomical classification is based on the level of selectivity, for example, organ-specific, cell-specific and organelle-specific. Mechanistic targeting can be distinguished based upon whether it is passive or active. Passive targeting utilizes the natural tendency of liposomes to distribute to cells of the reticulo-endothelial system (RES) in organs which contain sinusoidal capillaries. Active targeting, on the other hand, involves alteration of the liposome by coupling the liposome to a specific ligand such as a monoclonal antibody, sugar, glycolipid, or protein, or by changing the composition or size of the liposome in order to achieve targeting to organs and cell types other than the naturally occurring sites of localization.

The surface of the targeted delivery system may be modified in a variety of ways. In the case of a hyposomal targeted delivery system, lipid groups can be incorporated into the lipid bilayer of the liposome in order to maintain the targeting ligand in stable association with the liposomal bilayer. Various linking groups can be used for joining the lipid chains to the targeting ligand.

In general, the compounds bound to the surf ace of the targeted delivery system will be ligands and receptors which will allow the targeted delivery system to find and "home in" on the desired cells. A ligand may be any compound of interest which will bind to another compound, such as a receptor.

In general, surface membrane proteins which bind to specific effector molecules are referred to as receptors. In the present invention, antibodies of the invention are preferred receptors. Antibodies can be used to target liposomes to specific cell-surface ligands, in this case the peptides of choice. Preferably, the target tissue is lung tissue. A number of procedures can be used to covalently attach either poly-clonal or monoclonal antibodies to a liposome bilayer. Antibody-targeted liposomes can include mono-clonal or polygonal antibodies or fragments thereof such as Fab, or F(')2, as long as they bind efficiently to an the antigenic epitope on the target cells.

Preparations for parenteral administration include sterile aqueous or nonaqueous solutions, suspensions, and emulsions. Examples of non aqueous solvents are propylene glycol, polyethylene glycol, vegetable oils such as olive oil, and injectable organic esters such as ethyl oleate. Aqueous carriers include water, alcoholic/aqueous solutions, emulsions or suspensions, including saline and buffered media.

Parenteral vehicles include sodium chloride solution, Ringer's dextrose, dextrose and sodium chloride, lactated Ringer's intravenous vehicles include fluid and nutrient replenishers, electrolyte replenishers (such an those based on Ringer's dextrose), and the like. Preservatives and other additives may also be present such as, for example, antimicrobials, anti-oxidants, chelating agents and inert gases and the like.

The invention also relates to a method for preparing a medicament or pharmaceutical composition comprising the wildtype BMPR2 polypeptide of the invention, the medicament being used for therapy of pulmonary hypertension.

This invention will be better understood from the Experimental Details that follow. However, one skilled in the art will readily appreciate that the specific methods and results discussed are merely illustrative of the invention as described more fully in the claims that follow thereafter.

Experimental Details

Familial Primary Pulmonary Hypertension is a rare autosomal dominant disorder with reduced penetrance that has been mapped to a 3-centimorgan region on chromosome 2q34 (PPH1 locus). The phenotype is characterized by monoclonal plexiform lesions of proliferating endothelial cells in pulmonary arterioles that lead to elevated pulmonary artery pressures, right ventricular failure, and death. Although PPH is rare, cases secondary to known etiologies are more common and include those associated with the appetite suppressant drugs, including phentermine-fenfluramine. We genotyped 35 multiplex families with the disorder using 27 microsatellite markers, constructed disease haplotypes, and looked for evidence of haplotype sharing across families using the program TRANSMIT. Suggestive evidence of sharing was observed using markers GGAA19e07 and D2S307, and three nearby candidate genes were examined by dHPLC using individuals from 19 families. One of these genes (BMPR2), which encodes the bone morphogenetic protein receptor-II (BMPR-II), was found to contain 5 mutations that predict premature termination of the protein product and 2 missense mutations. These mutations were not observed in 196 control chromosomes. These findings indicate that the BMP signaling pathway is defective in patients with PPH and may implicate the pathway in the non-familial forms of the disease.

We have collected a number of multiplex families with PPH using experimental protocols approved by the Institutional Review Board of Columbia University College of Physicians and Surgeons. Methods used for clinical examination, as well as the diagnostic criteria, have been described elsewhere (Morse et al. 1997). Using DNA that was extracted from whole-blood samples or formalin-fixed, paraffinembedded tissue we genotyped 35 of these families (72 affected and 319 normals and carriers) using 27 microsatellite markers located in the 3-centimorgan minimal genetic region as previously described (Deng et al. 2000). Using the genetic model and marker order determined by radiation hybrid mapping (Deng et al. 2000), a 10-marker multipoint analysis using GENEHUNTER 2.0 (Kruglyak et al. 1996), gave a nearly constant 10d score of 10 across the region (data not shown). The maximum 10d scores of the 2point analyses, using MLINK from FASTLINK v4.1p (Cottingham, Jr., Idury, and Schaffer 1993), at a recombination fraction of zero were more variable, ranging from 0.6 to 8.6, with the higher scores clustering towards the telomeric end (data not shown). Given the low prevalence of the disorder and that some of the families were from a common founder, we reconstructed the 27-marker microsatellite disease haplotype from each when possible and visually inspected them for shared segments. No obvious shared DNA segments were found, so we used the haplotype analysis program, TRANSMIT v2.5 1999 (Clayton 1999), to look in a more rigorous fashion. Suggestive evidence of sharing (p=0.07) was found with the 345/214 base pair haplotype of markers GGAA19eO7 and D2S307. Since these markers were in the telomeric cluster we began our mutation scan in this region.

We investigated the genetic variation in the coding sequence of three nearby candidate genes by examining in 22 individuals from the 19 FPPH families and 2 normal controls using dHPLC with a WAVE® Nucleic Acid Fragment Analysis System from Transgenomics, Inc. (Omaha, Nebr.), as per the manufacturers directions and as described (Underhill et al. 1997; O'Donovan et al. 1998). These individuals were chosen on the basis of the amount of DNA available. PCR amplification products (max size=602 bp) were run with up to three melting profiles for fragments with multiple melting domains. DNA sequence determination of fragments containing potential variants were performed by cycle sequencing using Big Dyea terminators from Applied BioSystems Inc., (Foster City, Calif.) and sequencing products were resolved on Long Rangera gels (BioWhittaker Molecular Applications, Rockland, Me.) and detected with an ABI Model 377 DNA sequencer (ABI, Foster City, Calif.). DNA sequence traces were analyzed using Vector NTI suite 5.5 (Informax Inc., Bethesda, Md.). The first two genes, CD28 and CTLA4, were candidates due to their involvement in immune system regulation (Morse and Barst 1994). No variation in CD28 was observed. In CTLA4, we found one previously unreported SNP (49A>G) with an allele frequency of 0.50 that causes a non-conservative change in protein structure (A17T). It was homozygous in some of the patients and one of the controls and was ruled out as a potential disease mutation.

The third positional candidate, the gene encoding the bone morphogenetic protein receptor-II (BMPR2, also known as T-ALK, CL4-1 and BRK-3), a member of the TGF-b receptor superfamily, was suggested by the role of the BMP signaling pathway in lung morphogenesis (Warburton et al. 2000). The CDNA sequence of this approximately 4 kilobase gene encoding a 1038 amino acid protein had been previously described (Kawabata, Chytil, and Moses 1995; Liu et al. 1995; Rosenzweig et al. 1995; Nohno et al. 1995). To deduce the genomic structure of BMPR2 (FIGS. 1 and 2) we found homologous genomic sequences to exons 1, and 8–13 by querying the NCBI high-throughput genome sequence (HTGS) database using BLAST (Altschul et al. 1990). The intron size and DNA sequence of the other intron-exon boundaries were determined by amplifying and sequencing PCR products using oligonucleotide primers designed to amplify across neighboring exons, or out to a nearby Alu repeats, using the structure of mouse BMPR2 (Beppu et al. 1997) as a guide. We then designed oligonucleotide primers to amplify the exons from genomic DNA of the patients. These PCR fragments were screened by dHPLC and the DNA sequence of those containing apparent variation was determined. We observed mutations that are likely to disrupt the function of the receptor in 9 of the 19 families screened. Five of these predict premature termination of BMPR-II in exons 4, 6, 8 and 12, and each was only seen in one family (table 1 and FIG. 2). In addition, a SNP in exon 11 that causes a non-conservative change in amino acid sequence, from an arginine, conserved in all known type II TGF-b superfamily receptors (FIG. 3), to tryptophan was seen in three families (Table 1 and FIG. 2). The same arginine was changed to glutamine in another family (PPH019), but both parents were genotypically normal. The observation of this new mutation suggests that sporadic cases of PPH might also be caused by mutations in BMPR2. Except for this family, the expected pattern of mutations was observed when all additional members of the other 8 families were screened using dHPLC and DNA sequencing. None of the putative mutations were observed in 96 additional samples (196 chromosomes total). Applying Fisher's exact test to the data for all nine mutations, we observed a significant difference (p-value <0.0001) in mutation rate between cases and controls. We also observed a synonymous SNP (2811G>A) with a minor allele frequency of 21% in both samples.

The mutation in exon 4 is in the transmembrane domain and those in exons 6, 8 and 11 are in the kinase domain of this serine/threonine kinase receptor (FIG. 2). By analogy to studies of the TbR-II gene product (Wieser et al. 1993), at least three of these mutations (exons 4, 6 and 8) should encode a non-functional receptor that is unable to phosphorylate a type-I receptor and propagate the signal from a BMP ligand. The two mutations in exon 11 change Arg491. Since it is highly conserved and arginine is the most frequently changed amino acid in disease mutations (Human Gene Mutation Database), Arg491 is probably important to the function of BMPR-II. The mutations in exon 12 occur in the intracellular C-terminal domain of unknown function that is unique to BMPR-II.

We screened the entire publicly available coding sequence of BMPR2, but failed to find a causative mutation in 10 of the 19 families. The microsatellite data are consistent, but not conclusive, with linkage to PPH1 in all 19, but it is possible that the families with little linkage information could be unlinked to 2q34 and may have mutations in other genes in the BMP signaling pathway. However, several of the linked families are large (individual 10d scores >2), suggesting that we have not screened the entire gene. MRNA transcripts of 5, 6.5, 8 and 11.5 kb have been observed on Northern blots, with the longest transcript predominating in lung (Kawabata, Chytil, and Moses 1995; Rosenzweig et al. 1995; Nohno et al. 1995), so we may have missed some alternatively spliced exons in our screen. In addition, there is a $(GGC)_{12}$ trinucleotide repeat at the 5' end of the gene, at positions −928 to −963. This repeat is polymorphic in our families. Using PCR, we have not observed evidence of expansion of the repeat that would be consistent with the suggestion of anticipation in PPH (Loyd et al. 1995), but detection of this event might require a Southern blot and we have a limited quantity of DNA from the affected individuals (deceased) in many of our families.

So how do these mutations cause PPH? It is unlikely that they act as a dominant-negative by inhibiting apoptotic effect of the TGF-b pathway because BMPR-II does not associate with type-I receptors of the TGF-b family in transient expression assays using mammalian cells (Liu et al. 1995), even though this occurs in vitro (Kawabata, Chytil, and Moses 1995; Liu et al. 1995; Nohno et al. 1995). As would be predicted from what is known about the role of the BMP signaling pathway in early development, mice homozygous for a mutation in the kinase domain of BMPR2 die at day 9.5, prior to gastrulation (heterozygotes are grossly normal) (Beppu et al. 2000), so this function of the pathway must be functioning in patients with PPH. The BMP pathway induces apoptosis in some cell types (Soda et al. 1998; Kimura et al. 2000), so a partial block of signal transmission by haplo-insufficiency of BMPR-II might have a slow proliferative effect. BMP signaling may occur through both the Smad (Massague 1998) and mitogenactivated protein kinase (MAPK) (Kimura et al. 2000) cascades and both are inhibited by Smad6, which can be induced by vascular shear stress (Topper et al. 1997). The reduced apoptotic signals from the BMP pathway, caused by either mutations in BMPR2, other molecules in the signaling cascades (by analogy to hereditary hemorrhagic telangiectasia (Massague 1998)), or shear stress via Smad6, possibly after an initial nidus of vascular injury, might underlie many forms of PPH, including those associated with HIV or appetite suppressant drugs.

REFERENCES

1. Abenhaim L, Moride Y, Brenot F, Rich S, Benichou J, Kurz X, Higenbottam T, Oakley C, Wouters E, Aubier M, Simonneau G, Begaud B (1996) Appetite-suppressant drugs and the risk of primary pulmonary hypertension. International Primary Pulmonary Hypertension Study Group. N Engl J Med 335 (9):609–616
2. Altschul S F, Gish W, Miller W, Myers E W, Lipman D J (1990) Basic local alignment search tool. J Mol Biol 215 (3):403–410
3. Barst R J, Rubin L J, Long W A, McGoon M D, Rich S, Badesch D B, Groves B M, Tapson V F, Bourge R C, Brundage B H (1996) A comparison of continuous intravenous epoprostenol (prostacyclin) with conventional therapy for primary pulmonary hypertension. The Primary Pulmonary Hypertension Study Group. N Engl J Med 334 (5):296–302
4. Beppu H, Kawabata M, Hamamoto T, Chytil A, Minowa O, Noda T, Miyazono K (2000) BMP type II receptor is required for gastrulation and early development of mouse embryos. Dev Biol 221 (1):249–258
5. Beppu H, Minowa O, Miyazono K, Kawabata M (1997) cDNA cloning and genomic organization of the mouse BMP type II receptor. Biochem Biophys Res Commun 235 (3):499–504 n
6. Clayton D (1999) A Generalization of the Transmission/Disequilibrium Test for Uncertain-Haplotype Transmission. Am J Hum Genet 65 (4):1170–1177
7. Cottingham R W, Jr., Idury R M, Schaffer A A (1993) Faster sequential genetic linkage computations. Am J Hum Genet 53:252–263
8. D'Alonzo G E, Barst R J, Ayres S M, Bergofsky E H, Brundage B H, Detre K M, Fishman A P, Goldring R M, Groves B M, Kernis J T (1991) Survival in patients with primary pulmonary hypertension. Results from a national prospective registry. Ann Intern Med 115 (5):343–349
9. Deng Z, Haghighi F, Helleby L, Vanterpool K, Horn E M, Barst R J, Hodge S E, Morse J H, Knowles J A (2000) Fine mapping of PPH1, a gene for familial primary pulmonary hypertension, to a 3-cM region on chromosome 2q33. Am J Respir Crit Care Med 161 (3 Pt 1):1055–1059
10. Douglas J G, Munro J F, Kitchin A H, Muir A L, Proudfoot A T (1981) Pulmonary hypertension and fenfluramine. Br Med J (Clin Res Ed) 283 (6296):881–883
11. Kawabata M, Chytil A, Moses H L (1995) Cloning of a novel type II serine/threonine kinase receptor through interaction with the type I transforming growth factor-beta receptor. J Biol Chem 270 (10):5625–5630
12. Kimura N, Matsuo R, Shibuya H, Nakashima K, Taga T (2000) BMP2-induced Apoptosis Is Mediated by Activation of the TAK1-p38 Kinase Pathway That Is Negatively Regulated by Smad6. J Biol Chem 275 (23):17647–17652
13. Kruglyak L, Daly M J, Reeve-Daly M P, Lander E S (1996) Parametric and nonparametric linkage analysis: a unified multipoint approach. Am J Hum Genet 58 (6):1347–1363
14. Lee S D, Shroyer K R, Markham N E, Cool C D, Voelkel N F, Tuder R M (1998) Monoclonal endothelial cell proliferation is present in primary but not secondary pulmonary hypertension. J Clin Invest 101 (5):927–934
15. Liu F, Ventura F, Doody J, Massague J (1995) Human type II receptor for bone morphogenic proteins (BMPs) extension of the two-kinase receptor model to the BMPs. Mol Cell Biol 15 (7):3479–3486
16. Loyd J E, Butler M G, Foroud T M, Conneally P M, Phillips J A, Newman J H (1995) Genetic anticipation and abnormal gender ratio at birth in familial primary pulmonary hypertension. Am J Respir Crit Care Med 152 (1):93–97
17. Massague J (1998) TGF-beta signal transduction. Annu Rev Biochem 67:753–791
18. Morse J H and Barst R J (1994) Immunological disturbances in primary pulmonary hypertension. Sem Resp Crit Care 15:222–229
19. Morse J. H., Jones, A., DiBenedetto, A., Hodge, S. E., and Nygaard, T. G. (1996) Genetic mapping of primary pulmonary hypertension: Evidence for linkage to chromosome 2 in a large family. Circulation 94 (8):I-46
20. Morse J H, Jones A C, Barst R J, Hodge S E, Wilhelmsen K C, Nygaard T G (1997) Mapping of familial primary pulmonary hypertension locus (PPHl) to chromosome 2q31–q32. Circulation 95 (12):2603–2606
21. Nichols W C, Koller D L, Slovis B, Foroud T, Terry V H, Arnold N D, Siemieniak D R, Wheeler L, Phillips J A, Newman J H, Conneally P M, Ginsburg D, Loyd J E (1997) Localization of the gene for familial primary pulmonary hypertension to chromosome 2q31-32. Nat Genet 15 (3):277–280
22. Nohno T, Ishikawa T, Saito T, Hosokawa K, Noji S, Wolsing D H, Rosenbaum J S (1995) Identification of a human type II receptor for bone morphogenetic protein-4 that forms differential heteromeric complexes with bone morphogenetic protein type I receptors. J Biol Chem 270 (38):22522–22526
23. O'Donovan M C, Oefner P J, Roberts S C, Austin J, Hoogendoorn B, Guy C, Speight G, Upadhyaya M, Sommer SS, McGuffin P (1998) Blind Analysis of Denaturing High-Performance Liquid Chromatography as a Tool for Mutation Detection. Genomics 52 (1):44–49
24. Pasque M K, Trulock E P, Cooper J D, Triantafillou A N, Huddleston C B, Rosenbloom M, Sundaresan S, Cox J L, Patterson G A (1995) Single lung transplantation for pulmonary hypertension. Single institution experience in 34 patients. Circulation 92 (8):2252–2258
25. Rich S, Dantzker D R, Ayres S M, Bergofsky E H, Brundage B H, Detre K M, Fishman A P, Goldring R M, Groves B M, Koerner S K (1987) Primary pulmonary hypertension. A national prospective study. Ann Intern Med 107 (2):216223
26. Rosenzweig B L, Imamura T, Okadome T, Cox G N, Yamashita H, ten Dijke P, Heldin C H, Miyazono K (1995) Cloning and characterization of a human type II receptor for bone morphogenetic proteins. Proc Natl Acad Sci USA 92 (17):7632–7636
27. Soda H, Raymond E, Sharma S, Lawrence R, Cerna C, Gomez L, Timony G A, Von Hoff D D, Izbicka E (1998) Antiproliferative effects of recombinant human bone morphogenetic protein-2 on human tumor colony-forming units. Anticancer Drugs 9 (4):327–331
28. Topper J N, Cai J, Qiu Y, Anderson K R, Xu Y Y, Deeds J D, Feeley R, Gimeno C J, Woolf E A, Tayber O, Mays G G, Sampson B A, Schoen F J, Gimbrone M A, Jr., Falb D (1997) Vascular MADs: two novel MAD-related genes selectively inducible by flow in human vascular endothelium. Proc Natl Acad Sci USA 94 (17):9314–9319
29. Underhill P A, Jin L, Lin A A, Mehdi S Q, Jenkins T, Vollrath D, Davis R W, Cavalli-Sforza L L, Oefner P J (1997) Detection of numerous Y chromosome biallelic polymorphisms by denaturing high-performance liquid chromatography. Genome Res 7 (10):996–1005
30. Warburton D, Schwarz M, Tefft D, Flores-Delgado G, Anderson K D, Cardoso W V (2000) The molecular basis of lung morphogenesis. Mech Dev 92 (1):55–81
31. Wieser R, Attisano L, Wrana J L, Massague J (1993) Signaling activity of transforming growth factor beta type II receptors lacking specific domains in the cytoplasmic region. Mol Cell Biol 13 (12):7239–7247
32. Galloway, S. M., McNatty, K. P., Cambridge, L. M., Laitinen, M. P., Juengel, J. L., Jokiranta, T. S., McLaren, R. J., Luiro, K., Dodds, K. G., Montgomery, G. W., Beattie, A. E., Davis, G. H., and Ritvos, O. (2000). Mutations in an oocyte-derived growth factor gene (BMP15) cause increased ovulation rate and infertility in a dosage-sensitive manner [In Process Citation] Nat. Genet. 25, 279–283.
33. Morse, J. H. and Barst, R. J. (1997). Detection of familial primary pulmonary hypertension by genetic testing [letter]. N. Engl. J. Med. 337, 202–203.

What is claimed:

1. A method of detecting whether a subject is predisposed to, or afflicted with, a pulmonary hypertension which comprises (A) obtaining a suitable sample comprising a nucleic acid encoding bone morphogenetic protein receptor II from the subject; and (B) detecting in the nucleic acid encoding bone morphogenetic protein receptor II whether a mutation is present which is not present in a nucleic acid encoding wildtype bone morphogenetic protein receptor-II, wherein the mutation described relative to a difference from the sequence encoding wildtype bone morphogenetic protein receptor II set forth in SEQ ID NO:1 is selected from the group consisting of:

(1) a deletion of nucleotides having the sequence guanosine-guanosine-guanosine-guanosine-adenosine located at positions 1099–1103;

(2) a deletion of a thymidine nucleotide located at position 2579;

(3) a substitution of nucleotides having the sequence cytosine-thymidine-thymidine-thymidine located at positions 507–510 with nucleotides having the sequence adenosine-adenosine-adenosine;

(4) a substitution of a cytosine nucleotide located at position 2617 with a thymidine nucleotide;

(5) a substitution of nucleotides having the sequence adenosine-guanosine located at positions 690–691 with a thymidine nucleotide;

(6) a substitution of a cytosine nucleotide located at position 1471 with a thymidine nucleotide;

(7) a substitution of a guanosine nucleotide located at position 1472 with an adenosine nucleotide;

(8) a deletion of nucleotides having the sequence adenosine-thymidine-thymidine-thymidine located at positions 1248–1251;

(9) a substitution of a cytosine nucleotide located at position 994 with a thymidine;

(10) a substitution of a thymidine nucleotide located at position 295 with a cytosine nucleotide;

(11) a deletion of a guanosine nucleotide located at position 1097;

(12) a substitution of a guanosine nucleotide located at position 727 with a thymidine nucleotide;

(13) a deletion of an adenosine nucleotide located at position 1214;

(14) a deletion of nucleotides having the sequence adenosine-cytosine located at positions 2441–2442;

(15) a substitution of a cytosine nucleotide located at position 2695 with a thymidine nucleotide;

(16) a deletion of 21 nucleotides located at positions 189–209;

(17) a substitution of a guanosine nucleotide located at position 296 with an adenosine nucleotide;

(18) a substitution of a thymidine nucleotide located at position 250 with a cytosine nucleotide;

(19) a substitution of a guanosine nucleotide located at position 1040 with an adenosine nucleotide;

wherein the presence of such a mutation indicates that the subject is predisposed, to or afflicted with, the pulmonary hypertension.

2. A method of detecting whether a subject is predisposed to, or afflicted with, a pulmonary hypertension which comprises (A) obtaining a suitable sample comprising bone morphogenetic protein receptor II from the subject; and (B) detecting in the bone morphogenetic protein receptor II whether a mutation is present which is not present in wildtype bone morphogenetic protein receptor-II, wherein the mutation described relative to a difference from the wildtype bone morphogenetic protein receptor II sequence set forth in SEQ ID NO:2 is selected from the group consisting of:

(1) a mutation at a glutamic acid residue located at position 368 which causes the protein sequence thereon to be different from the wildtype bone morphogenetic protein receptor II sequence;

(2) a mutation at an asparagine residue located at position 861 which causes the protein sequence thereon to be different from the wildtype bone morphogenetic protein receptor II sequence;

(3) a substitution of a cysteine residue located at position 169 which causes premature termination of the protein sequence;

(4) a substitution of an arginine residue located at position 873 which causes premature termination of the protein sequence;

(5) a mutation at a lysine residue located at position 230 which causes the protein sequence thereon to be different from the wildtype bone morphogenetic protein receptor II sequence;

(6) a substitution of an arginine residue located at position 491 with a tryptophan residue;

(7) a substitution of an arginine residue located at position 491 with a glutainine residue;

(8) a substitution of a phenylalanine residue located at position 417 which causes premature termination of the protein sequence;

(9) a substitution of an arginine residue located at position 332 which causes premature termination of the protein sequence;

(10) a substitution of a cysteine residue located at position 99 with an arginine residue;

(11) a mutation at a proline residue located at position 366 which causes the protein sequence thereon to be different from the wildtype bone morphogenetic protein receptor II sequence;

(12) a substitution of a glutainic acid residue located at position 243 which causes premature termination of the protein sequence;

(13) a mutation at an aspartic acid residue located at position 405 which causes the protein sequence thereon to be different from the wildtype bone morphogenetic protein receptor II sequence;

(14) a mutation at a histidine residue located at position 814 which causes the protein sequence thereon to be different from the wildtype bone morphogenetic protein receptor II sequence;

(15) a substitution of an arginine residue located at position 899 which causes premature termination of the protein sequence;

(16) a deletion of consecutive amino acids having the sequence serine-leucine-tryptophan located at positions 64–70;

(17) a substitution of a cysteine residue located at position 99 with a tyrosine residue;

(18) a substitution of a cysteine residue located at position 84 with an arginine residue;

(19) a substitution of a cysteine residue located at position 347 with a tyrosine residue;

wherein the presence of such a mutation indicates that the subject is predisposed, to or afflicted with, the pulmonary hypertension.

3. The method of claim 1, wherein the pulmonary hypertension is Primary Pulmonary Hypertension.

4. The method of claim 3, wherein the Primary Pulmonary Hypertension is Familial Primary Pulmonary Hypertension.

5. A method of detecting whether a subject is either predisposed to, or afflicted with, Familial Primary Pulmonary Hypertension which comprises:

a) obtaining a suitable nucleic acid sample from the subject; and b) detecting the presence of a $(GGC)_{12}$ trinucleotide repeat at positions corresponding to positions −928 to −963 in the 5'end of the subject's bone morphogenetic protein receptor-II gene, wherein the presence of the trinucleotide repeat indicates that the subject is either predisposed to, or afflicted with, Familial Primary Pulmonary Hypertension.

* * * * *

SEQUENCE LISTING

<160> NUMBER OF SEQ ID NOS: 30

<210> SEQ ID NO 1
<211> LENGTH: 6234
<212> TYPE: DNA
<213> ORGANISM: Human

<400> SEQUENCE: 1

```
atgacttcct cgctgcagcg gccctggcgg gtgccctggc taccatggac tactgaagga      60
gcgacgtcgc cgggaccgcc cacgggaccg atggtacctg catcctgctg gtcagcactg     120
cggctgcttc gcagaatcaa gaacggctat gtaggacgac cagtcgtgac gccgacgaag     180
cgtcttagtt cttgccgata gtgcgtttaa agatccgtat cagcaagacc ttgggatagg     240
tgagagtaga cacgcaaatt tctaggcata gtcgttctgg aaccctatcc actctcatct     300
atctctcatg aaaatgggac aatattatgc tcgaaaggta gcacctgcta tagagagtac     360
ttttaccctg ttataatacg agctttccat cgtggacgat tggcctttgg gagaaatcaa     420 aagggacat  aaatcttgta aaacaaggat accggaaacc ctctttagtt ttcccctgta     480
tttagaacat tttgttccta gttggtctca cattggagat ccccaagagt gtcactatga     540
agaatgtgta caaccagagt gtaacctcta ggggttctca cagtgatact tcttacacat     600
gtaactacca ctcctccctc aattcagaat ggaacatacc gtttctgctg cattgatggt     660
gaggagggag ttaagtctta ccttgtatgg caaagacgac ttgtagcaca gatttatgta     720
atgtcaactt tactgagaat tttccacctc aacatcgtgt ctaaatacat tacagttgaa     780
atgactctta aaggtggag  ctgacacaac accactcagt ccacctcatt catttaaccg     840
agatgagaca gactgtgttg tggtgagtca ggtggagtaa gtaaattggc tctactctgt     900
ataatcattg ctttggcatc agtctctgta ttagctgttt tgatagttgc tattagtaac     960
gaaaccgtag tcagagacat aatcgacaaa actatcaacg cttatgcttt ggatacagaa    1020
tgttgacagg agaccgtaaa caaggtcttc gaatacgaaa cctatgtctt acaactgtcc    1080
tctggcattt gttccagaag acagtatgaa catgatggag gcagcagcat ccgaaccctc    1140
tcttgatcta tgtcatactt gtactacctc cgtcgtcgta ggcttgggag agaactagat    1200
gataatctga aactgttgga gctgattggc cgaggtcgat atggagcagt ctattagact    1260
ttgacaacct cgactaaccg gctccagcta tacctcgtca atataaaggc tccttggatg    1320
agcgtccagt tgctgtaaaa gtgttttcct tatatttccg aggaacctac tcgcaggtca    1380
acgacatttt cacaaaagga ttgcaaaccg tcagaatttt atcaacgaaa agaacattta    1440
cagagtgcct aacgtttggc agtcttaaaa tagttgcttt tcttgtaaat gtctcacgga    1500
ttgatggaac atgacaacat tgcccgcttt atagttggag atgagagagt aactaccttg    1560
```

-continued

```
tactgttgta acgggcgaaa tatcaacctc tactctctca cactgcagat ggacgcatgg    1620
aatatttgct tgtgatggag tactatccca gtgacgtcta cctgcgtacc ttataaacga    1680
acactacctc atgatagggt atggatcttt atgcaagtat ttaagtctcc acacaagtga    1740
ctgggtaagc tacctagaaa tacgttcata aattcagagg tgtgttcact gacccattcg    1800
tcttgccgtc ttgctcattc tgttactaga ggactggctt atcttcacac agaacggcag    1860
aacgagtaag acaatgatct cctgaccgaa tagaagtgtg agaattacca cgaggagatc    1920
attataaacc tgcaatttcc catcgagatt tcttaatggt gctcctctag taatatttgg    1980
acgttaaagg gtagctctaa taaacagcag aaatgtccta gtgaaaaatg atggaacctg    2040
tgttattagt atttgtcgtc tttacaggat cacttttttac taccttggac acaataatca    2100
gactttggac tgtccatgag gctgactgga aatagactgg tgcgcccagg ctgaaacctg    2160
acaggtactc cgactgacct ttatctgacc acgcgggtcc ggaggaagat aatgcagcca    2220
taagcgaggt tggcactatc agatatatgg cctccttcta ttacgtcggt attcgctcca    2280
accgtgatag tctatatacc caccagaagt gctagaagga gctgtgaact tgagggactg    2340
tgaatcagct gtggtcttca cgatcttcct cgacacttga actccctgac acttagtcga    2400
ttgaaacaag tagacatgta tgctcttgga ctaatctatt gggagatatt aactttgttc    2460
atctgtacat acgagaacct gattagataa ccctctataa tatgagatgt acagacctct    2520
tcccagggga atccgtacca gagtaccaga atactctaca tgtctggaga agggtcccct    2580
taggcatggt ctcatggtct tggcttttca gacagaggtt ggaaaccatc ccacttttga    2640
ggatatgcag accgaaaagt ctgtctccaa cctttggtag ggtgaaaact cctatacgtc    2700
gttctcgtgt ctagggaaaa acagagaccc aagttcccag aagcctggaa caagagcaca    2760 gatcccttt tgtctctggg ttcaagggtc ttcggacctt agaaaatagc ctggcagtga    2820
ggtcactcaa ggagacaatc gaagactgtt tcttttatcg gaccgtcact ccagtgagtt    2880
cctctgttag cttctgacaa gggaccagga tgcagaggct cggcttactg cacagtgtgc    2940
tgaggaaagg ccctggtcct acgtctccga gccgaatgac gtgtcacacg actcctttcc    3000
atggctgaac ttatgatgat ttgggaaaga acaaatctg tgagcccaac taccgacttg    3060
aatactacta aacccttcct tgttttagac actcgggttg agtcaatcca atgtctactg    3120
ctatgcagaa tgaacgcaac ctgtcacata tcagttaggt tacagatgac gatacgtctt    3180
acttgcgttg gacagtgtat ataggcgtgt gccaaaaatt ggtccttatc cagattattc    3240
ttcctcctca tatccgcaca cggttttttaa ccaggaatag gtctaataag aaggaggagt    3300
tacattgaag actctatcca tcatactgac agcatcgtga agaatatttc atgtaacttc    3360
tgagataggt agtatgactg tcgtagcact tcttataaag ctctgagcat tctatgtcca    3420 gcacacctttt gactataggg gaaaaaaacc gagactcgta agatacaggt cgtgtggaaa    3480
ctgatatccc cttttttttgg gaaattcaat taactatgaa cgacagcaag cacaagctcg    3540
aatccccagc ctttaagtta attgatactt gctgtcgttc gtgttcgagc ttaggggtcg    3600
cctgaaacaa gtgtcaccag cctctccacc aacacaacaa ccacaaacac ggactttgtt    3660
cacagtggtc ggagaggtgg ttgtgttgtt ggtgtttgtg cacaggactc acgccaagta    3720
ctggcatgac tactatatct gagatgccat gtgtcctgag tgcggttcat gaccgtactg    3780
atgatataga ctctacggta acccagatga aacaaatctg cataccacaa atgttgcaca    3840
gtcaattggg tgggtctact tgtttagac gtatggtgtt tacaacgtgt cagttaaccc    3900
```

-continued

```
ccaacccctg tctgcttaca gctgacagaa gaagacttgg aaaccaacaa ggttggggac    3960
agacgaatgt cgactgtctt cttctgaacc tttggttgtt gctagaccca aaagaagttg    4020
ataagaacct caaggaaagc tctgatgaga cgatctgggt tttcttcaac tattcttgga    4080
gttcctttcg agactactct atctcatgga gcactctctt aaacagttca gtggcccaga    4140
cccactgagc tagagtacct cgtgagagaa tttgtcaagt caccgggtct gggtgactcg    4200
agtactagtt ctagcttgct ttacccactc ataaaacttg cagtagaagc tcatgatcaa    4260
gatcgaacga aatgggtgag tattttgaac gtcatcttcg aactggacag caggacttca    4320
cacagactgc aaatggccaa gcatgtttga ttgacctgtc gtcctgaagt gtgtctgacg    4380
tttaccggtt cgtacaaact ttcctgatgt tctgcctact cagatctatc ctctccccaa    4440
gcagcagaac aaggactaca agacggatga gtctagatag gagagggtt cgtcgtcttg    4500 cttcccaaga gacctactag tttgcctttg aacaccaaaa attcaacaaa gaagggttct    4560
ctggatgatc aaacgaaac ttgtggtttt taagttgttt agagcccgg ctaaaatttg    4620 gcagcaagca caaatcaaac ttgaaacaag tctcggggcc gattttaaac cgtcgttcgt    4680
gtttagtttg aactttgttc tcgaaactgg agttgccaag atgaatacaa tcaatgcagc    4740
agaacctcat agctttgacc tcaacggttc tacttatgtt agttacgtcg tcttggagta    4800
gtggtgacag tcaccatgaa tggtgtggca ggtagaaacc acagtgttaa caccactgtc    4860
agtggtactt accacaccgt ccatctttgg tgtcacaatt ctcccatgct gccacaaccc    4920
aatatgccaa taggacagta ctatctggcc gagggtacga cggtgttggg ttatacggtt    4980
atcctgtcat gatagaccgg aaacaaccaa catagtgaca catagggccc aagaaatgtt    5040
gcagaatcag tttgttggtt gtatcactgt gtatcccggg ttctttacaa cgtcttagtc    5100
tttattggtg aggacacccg gctgaatatt aattccagtc ctgatgagca aaataaccac    5160
tcctgtgggc cgacttataa ttaaggtcag gactactcgt tgagccttta ctgagacgag    5220
agcaacaagc tggccatgat gaaggtgttc actcggaaat gactctgctc tcgttgttcg    5280
accggtacta cttccacaag tggatcgtct tgtggacagg agggaacggc cactagaagg    5340
tggccgaact acctagcaga acacctgtcc tcccttgccg gtgatcttcc accggcttga    5400
aattccaata acaacaacag caatccatgt tcagaacaag atgttcttgc ttaaggttat    5460
tgttgttgtc gttaggtaca agtcttgttc tacaagaacg acagggtgtt ccaagcacag    5520
cagcagatcc tgggccatca aagcccagaa tgtcccacaa ggttcgtgtc gtcgtctagg    5580
acccggtagt ttcgggtctt gagcacagag gcctaattct ctggatcttt cagccacaaa    5640
tgtcctggat ctcgtgtctc cggattaaga gacctagaaa gtcggtgttt acaggaccta    5700
ggcagcagta tacagatagg tgagtcaaca caagatggca aatcaggatc ccgtcgtcat    5760
atgtctatcc actcagttgt gttctaccgt ttagtcctag aggtgaaaag atcaagaaac    5820
gtgtgaaaac tccctattct cttaagcggt tccacttttc tagttctttg cacacttttg    5880
agggataaga gaattcgcca ggcgcccctc cacctgggtc atctccactg aatcgctgga    5940
ctgtgaagtc ccgcggggag gtggaccccag tagaggtgac ttagcgacct gacacttcag    6000
aacaataatg gcagtaacag ggcagttcat tccaaatcca gcactgctgt tgttattac     6060 cgtcattgtc ccgtcaagta aggtttaggt cgtgacgaca ttaccttgca gaaggaggca    6120
ctgctacaac catggtgtct aaagatatag aatggaacgt cttcctccgt gacgatgttg    6180
gtaccacaga tttctatatc gaatgaactg tctgtgactt acttgacaga cact           6234
```

-continued

<210> SEQ ID NO 2
<211> LENGTH: 1080
<212> TYPE: PRT
<213> ORGANISM: Human

<400> SEQUENCE: 2

```
Met Thr Ser Ser Leu Gln Arg Pro Trp Arg Val Pro Trp Leu Pro Trp
1               5                   10                  15

Thr Thr Ile Leu Leu Val Ser Thr Ala Ala Ser Gln Asn Gln Glu
            20                  25                  30

Arg Leu Cys Cys Ala Phe Lys Asp Pro Tyr Gln Gln Asp Leu Gly Ile
            35                  40                  45

Gly Glu Ser Arg Ile Ser His Glu Asn Gly Thr Ile Leu Cys Ser Lys
    50                  55                  60

Gly Ser Thr Cys Tyr Tyr Gly Leu Trp Glu Lys Ser Lys Gly Asp Ile
65                  70                  75                  80

Asn Leu Val Lys Gln Gly Cys Cys Trp Ser His Ile Gly Asp Pro Gln
                85                  90                  95

Glu Cys His Tyr Glu Glu Cys Val Val Thr Thr Thr Pro Pro Ser Ile
            100                 105                 110

Gln Asn Gly Thr Tyr Arg Phe Cys Cys Cys Ser Thr Asp Leu Cys
            115                 120                 125

Asn Val Asn Phe Thr Glu Asn Phe Pro Pro Pro Asp Thr Thr Pro
130                 135                 140

Leu Ser Pro Pro His Ser Phe Asn Arg Asp Glu Thr Ile Ile Ala
145                 150                 155                 160

Leu Ala Ser Val Ser Val Leu Ala Val Leu Ile Val Ala Ala Leu Cys
                165                 170                 175

Phe Gly Tyr Arg Met Leu Thr Gly Asp Arg Lys Gln Gly Leu His His
            180                 185                 190

Ser Met Asn Met Met Glu Ala Ala Ser Glu Pro Ser Leu Asp Leu
        195                 200                 205

Asp Asn Leu Lys Leu Leu Glu Leu Ile Gly Arg Gly Arg Tyr Gly Ala
210                 215                 220

Val Val Tyr Lys Gly Ser Leu Asp Glu Arg Pro Val Ala Val Lys Val
225                 230                 235                 240

Phe Ser Phe Phe Ala Asn Arg Gln Asn Phe Ile Asn Glu Lys Asn Ile
                245                 250                 255

Tyr Arg Val Pro Leu Met Glu His Asp Asn Ile Ala Arg Phe Ile Val
            260                 265                 270

Gly Asp Glu Arg Val Val Thr Ala Asp Gly Arg Met Glu Tyr Leu Leu
        275                 280                 285

Val Met Glu Tyr Tyr Pro Asn Asn Gly Ser Leu Cys Lys Tyr Leu Ser
    290                 295                 300

Leu His Thr Ser Asp Trp Val Ser Ser Cys Arg Leu Ala His Ser Val
305                 310                 315                 320

Thr Arg Gly Leu Ala Tyr Leu His Thr Thr Glu Leu Pro Arg Gly Asp
                325                 330                 335

His Tyr Lys Pro Ala Ile Ser His Arg Asp Leu Leu Asn Ser Arg Asn
            340                 345                 350

Val Leu Val Lys Asn Asp Gly Thr Cys Val Ile Ser Asp Phe Gly Leu
        355                 360                 365

Ser Met Arg Leu Thr Gly Asn Arg Leu Val Arg Pro Gly Gly Glu Glu
    370                 375                 380
```

-continued

```
Asp Asn Ala Ala Ile Ser Glu Val Gly Thr Ile Arg Tyr Met Ala Ala
385                 390                 395                 400

Pro Glu Val Leu Glu Gly Ala Val Asn Leu Arg Asp Cys Glu Ser Ala
                405                 410                 415

Leu Lys Gln Val Asp Met Tyr Ala Leu Gly Leu Ile Tyr Trp Glu Ile
            420                 425                 430

Phe Phe Met Arg Cys Thr Asp Leu Phe Pro Gly Glu Ser Val Pro Glu
        435                 440                 445

Tyr Gln Met Met Ala Phe Gln Thr Glu Val Gly Asn His Pro Thr Phe
    450                 455                 460

Glu Asp Met Gln Val Leu Val Ser Arg Glu Lys Gln Arg Pro Lys Phe
465                 470                 475                 480

Pro Glu Ala Trp Lys Lys Glu Asn Ser Leu Ala Val Arg Ser Leu Lys
                485                 490                 495

Glu Thr Ile Glu Asp Cys Trp Trp Asp Gln Asp Ala Glu Ala Arg Leu
            500                 505                 510

Thr Ala Gln Cys Ala Glu Glu Arg Met Ala Glu Leu Met Met Ile Trp
        515                 520                 525

Glu Arg Asn Lys Ser Val Ser Pro Thr Thr Val Asn Pro Met Ser Thr
    530                 535                 540

Ala Met Gln Asn Glu Arg Asn Leu Ser His Asn Asn Arg Arg Val Pro
545                 550                 555                 560

Lys Ile Gly Pro Tyr Pro Asp Tyr Ser Ser Ser Tyr Ile Glu Asp
                565                 570                 575

Ser Ile His His Thr Asp Ser Ile Val Lys Asn Ile Ser Ser Glu His
            580                 585                 590

Ser Met Ser Ser Thr Pro Leu Thr Ile Gly Glu Lys Asn Arg Arg Asn
        595                 600                 605

Ser Ile Asn Tyr Glu Arg Gln Gln Ala Gln Ala Arg Ile Pro Ser Pro
    610                 615                 620

Glu Thr Ser Val Thr Ser Leu Ser Thr Asn Thr Thr Thr Asn Thr
625                 630                 635                 640

Thr Thr Gly Leu Thr Pro Ser Thr Gly Met Thr Thr Ile Ser Glu Met
                645                 650                 655

Pro Tyr Tyr Pro Asp Glu Thr Asn Leu His Thr Thr Asn Val Ala Gln
            660                 665                 670

Ser Ile Gly Pro Thr Pro Val Cys Leu Gln Leu Thr Glu Glu Asp Leu
        675                 680                 685

Glu Thr Asn Lys Lys Leu Asp Pro Lys Glu Val Asp Lys Asn Leu Lys
    690                 695                 700

Glu Ser Ser Asp Glu Asn Asn Leu Met Glu His Ser Leu Lys Gln Phe
705                 710                 715                 720

Ser Gly Pro Asp Pro Leu Ser Ser Thr Ser Ser Ser Leu Leu Tyr Pro
                725                 730                 735

Leu Ile Lys Leu Ala Val Glu Ala Ala Thr Gly Gln Gln Asp Phe
            740                 745                 750

Thr Gln Thr Ala Asn Gly Gln Ala Cys Leu Ile Ile Pro Asp Val Leu
        755                 760                 765

Pro Thr Gln Ile Tyr Pro Leu Pro Lys Gln Gln Asn Leu Pro Lys Arg
    770                 775                 780

Pro Thr Ser Leu Pro Leu Asn Thr Lys Asn Ser Thr Lys Lys Glu Pro
785                 790                 795                 800

Arg Leu Lys Phe Gly Ser Lys His Lys Ser Asn Leu Lys Gln Val Val
```

-continued

```
            805                 810                 815
Glu Thr Gly Val Ala Lys Met Asn Thr Ile Asn Ala Ala Glu Pro His
        820                 825                 830
Val Val Thr Val Thr Met Asn Gly Val Ala Gly Arg Asn His Ser Val
        835                 840                 845
Asn Asn Ser His Ala Ala Thr Thr Gln Tyr Ala Asn Arg Thr Val Leu
        850                 855                 860
Ser Gly Gln Gln Thr Thr Asn Ile Val Thr His Arg Ala Gln Glu Met
865                 870                 875                 880
Leu Gln Asn Gln Phe Ile Gly Glu Asp Thr Arg Leu Asn Ile Asn Ser
            885                 890                 895
Ser Pro Asp Glu His His Glu Pro Leu Leu Arg Arg Glu Gln Gln Ala
        900                 905                 910
Gly His Asp Glu Gly Val Leu Leu Asp Arg Leu Val Asp Arg Arg Glu
        915                 920                 925
Arg Pro Leu Glu Gly Gly Arg Thr Asn Ser Asn Asn Asn Ser Asn
        930                 935                 940
Pro Cys Ser Glu Gln Asp Val Leu Ala Ala Gln Gly Val Pro Ser Thr
945                 950                 955                 960
Ala Ala Asp Pro Gly Pro Ser Lys Pro Arg Arg Arg Ala Gln Arg Pro
            965                 970                 975
Asn Ser Leu Asp Leu Ser Ala Thr Asn Val Leu Asp Gly Ser Ser Ile
            980                 985                 990
Gln Ile Gly Glu Ser Thr Gln Asp  Gly Lys Ser Gly Ser  Ser Gly Glu
            995                 1000                1005
Lys Ile Lys Lys Arg Val Lys  Thr Pro Tyr Ser Leu  Lys Arg Trp
        1010                1015                1020
Trp Arg Pro Ser Thr Trp Val  Ile Ser Thr Glu Ser  Leu Asp Cys
        1025                1030                1035
Glu Val Asn Asn Asn Gly Ser  Asn Arg Ala Val His  Ser Lys Ser
        1040                1045                1050
Ser Thr Ala Val Val Thr Leu  Ala Glu Gly Gly Thr  Ala Thr Thr
        1055                1060                1065
Met Val Ser Lys Asp Ile Gly  Gly Met Asn Cys Leu
        1070                1075                1080
```

<210> SEQ ID NO 3
<211> LENGTH: 39
<212> TYPE: DNA
<213> ORGANISM: Human

<400> SEQUENCE: 3
gctggtgagt agctccggct ttcctttatt ttagcttcg           39

<210> SEQ ID NO 4
<211> LENGTH: 39
<212> TYPE: DNA
<213> ORGANISM: Human

<400> SEQUENCE: 4
caaggcaagt gatactttcc atattgattt ataggatat           39

<210> SEQ ID NO 5
<211> LENGTH: 39
<212> TYPE: DNA
<213> ORGANISM: Human

```
<400> SEQUENCE: 5
ctcagtaagt aaagtaacct ttgttttctt ttaggtcca                        39

<210> SEQ ID NO 6
<211> LENGTH: 39
<212> TYPE: DNA
<213> ORGANISM: Human

<400> SEQUENCE: 6
acaggtaaaa attaccattt tcctgttctt ataggagac                        39

<210> SEQ ID NO 7
<211> LENGTH: 42
<212> TYPE: DNA
<213> ORGANISM: Human

<400> SEQUENCE: 7
ttggaggtaa gtttgccgtt attaaaacac ttgcagctga tt                    42

<210> SEQ ID NO 8
<211> LENGTH: 42
<212> TYPE: DNA
<213> ORGANISM: Human

<400> SEQUENCE: 8
cccaatgtaa gttcttcata gttttcctct atagggat ct                      42

<210> SEQ ID NO 9
<211> LENGTH: 39
<212> TYPE: DNA
<213> ORGANISM: Human

<400> SEQUENCE: 9
ggaggtaaga tagtcaataa aattatccaa acagatcat                        39

<210> SEQ ID NO 10
<211> LENGTH: 42
<212> TYPE: DNA
<213> ORGANISM: Human

<400> SEQUENCE: 10
agcgaggtga gtgtatacaa aactctaatt tatcaggttg gc                    42

<210> SEQ ID NO 11
<211> LENGTH: 39
<212> TYPE: DNA
<213> ORGANISM: Human

<400> SEQUENCE: 11
ccaggtaaaa actactgtct ctacaaatcc acaggggaa                        39

<210> SEQ ID NO 12
<211> LENGTH: 42
<212> TYPE: DNA
<213> ORGANISM: Human

<400> SEQUENCE: 12
agcctggtaa gaaaaaacta atactttgtc ttacaggcag tg                    42

<210> SEQ ID NO 13
<211> LENGTH: 39
<212> TYPE: DNA
<213> ORGANISM: Human
```

<400> SEQUENCE: 13
gaacggtaag accctaaggg ctttctttct ttaagcaac            39

<210> SEQ ID NO 14
<211> LENGTH: 39
<212> TYPE: DNA
<213> ORGANISM: Human

<400> SEQUENCE: 14
cagagtaagt ggagggatcc acttttattt tcagtaggt            39

<210> SEQ ID NO 15
<211> LENGTH: 29
<212> TYPE: PRT
<213> ORGANISM: Human

<400> SEQUENCE: 15

Leu Lys Glu Thr Ile Glu Asp Cys Trp Asp Gln Asp Ala Glu Ala Trp
1               5                   10                  15

Leu Thr Ala Gln Cys Ala Glu Glu Arg Met Ala Glu Leu
            20                  25

<210> SEQ ID NO 16
<211> LENGTH: 29
<212> TYPE: PRT
<213> ORGANISM: Homo sapiens

<400> SEQUENCE: 16

Leu Lys Glu Thr Ile Glu Asp Cys Trp Asp Gln Asp Ala Glu Ala Arg
1               5                   10                  15

Leu Thr Ala Gln Cys Ala Glu Glu Arg Met Ala Glu Leu
            20                  25

<210> SEQ ID NO 17
<211> LENGTH: 29
<212> TYPE: PRT
<213> ORGANISM: Mus musculus

<400> SEQUENCE: 17

Leu Lys Glu Thr Ile Glu Asp Cys Trp Asp Gln Asp Ala Glu Ala Arg
1               5                   10                  15

Leu Thr Ala Gln Cys Ala Glu Glu Arg Met Ala Glu Leu
            20                  25

<210> SEQ ID NO 18
<211> LENGTH: 29
<212> TYPE: PRT
<213> ORGANISM: Xenopus laevis

<400> SEQUENCE: 18

Leu Lys Glu Thr Ile Asp Asp Cys Trp Asp Gln Asp Ala Glu Ala Arg
1               5                   10                  15

Leu Thr Ala Gln Cys Ala Glu Glu Arg Met Ala Glu Leu
            20                  25

<210> SEQ ID NO 19
<211> LENGTH: 29
<212> TYPE: PRT
<213> ORGANISM: Gallus gallus

<400> SEQUENCE: 19

```
Leu Lys Glu Thr Ile Glu Asp Cys Trp Asp Gln Asp Ala Glu Ala Arg
1               5                   10                  15

Leu Thr Ala Gln Cys Ala Glu Glu Arg Met Ala Glu Leu
            20                  25
```

<210> SEQ ID NO 20
<211> LENGTH: 29
<212> TYPE: PRT
<213> ORGANISM: Home sapiens

<400> SEQUENCE: 20

```
Val Cys Glu Thr Leu Thr Glu Cys Trp Asp His Asp Pro Glu Ala Arg
1               5                   10                  15

Leu Thr Ala Gln Cys Val Ala Glu Arg Phe Ser Glu Leu
            20                  25
```

<210> SEQ ID NO 21
<211> LENGTH: 29
<212> TYPE: PRT
<213> ORGANISM: Mus musculus

<400> SEQUENCE: 21

```
Val Cys Glu Thr Leu Thr Glu Cys Trp Asp His Asp Pro Glu Ala Arg
1               5                   10                  15

Leu Thr Ala Gln Cys Val Ala Glu Arg Phe Ser Glu Leu
            20                  25
```

<210> SEQ ID NO 22
<211> LENGTH: 29
<212> TYPE: PRT
<213> ORGANISM: Rattus Norvegicus

<400> SEQUENCE: 22

```
Val Cys Glu Thr Leu Thr Glu Cys Trp Asp His Asp Pro Glu Ala Arg
1               5                   10                  15

Leu Thr Ala Gln Cys Val Ala Glu Arg Phe Ser Glu Leu
            20                  25
```

<210> SEQ ID NO 23
<211> LENGTH: 29
<212> TYPE: PRT
<213> ORGANISM: Homo sapiens

<400> SEQUENCE: 23

```
Leu Cys Val Thr Ile Glu Asp Cys Trp Asp His Asp Ala Glu Ala Arg
1               5                   10                  15

Leu Ser Ala Gly Cys Val Glu Glu Arg Val Ser Leu Ile
            20                  25
```

<210> SEQ ID NO 24
<211> LENGTH: 29
<212> TYPE: PRT
<213> ORGANISM: sheep

<400> SEQUENCE: 24

```
Leu Cys Glu Thr Ile Glu Glu Cys Trp Asp His Asp Ala Glu Ala Arg
1               5                   10                  15

Leu Ser Ala Gly Cys Val Gly Glu Arg Ile Thr Gln Met
            20                  25
```

<210> SEQ ID NO 25
<211> LENGTH: 29

```
<212> TYPE: PRT
<213> ORGANISM: Gallus gallus

<400> SEQUENCE: 25

Leu Cys Glu Thr Ile Glu Glu Cys Trp Asp His Asp Ala Glu Ala Arg
1               5                   10                  15

Leu Ser Ala Gly Cys Val Glu Glu Arg Ile Ile Gln Met
            20                  25

<210> SEQ ID NO 26
<211> LENGTH: 29
<212> TYPE: PRT
<213> ORGANISM: Homo sapiens

<400> SEQUENCE: 26

Leu Arg Glu Leu Leu Glu Asp Cys Trp Asp Ala Asp Pro Glu Ala Arg
1               5                   10                  15

Leu Thr Ala Glu Cys Val Gln Gln Arg Leu Ala Ala Leu
            20                  25

<210> SEQ ID NO 27
<211> LENGTH: 29
<212> TYPE: PRT
<213> ORGANISM: Rattus Norvegicus

<400> SEQUENCE: 27

Leu Arg Glu Leu Leu Glu Asp Cys Trp Asp Ala Asp Pro Glu Ala Arg
1               5                   10                  15

Leu Thr Ala Glu Cys Val Gln Gln Arg Leu Ala Ala Leu
            20                  25

<210> SEQ ID NO 28
<211> LENGTH: 29
<212> TYPE: PRT
<213> ORGANISM: C.elegans

<400> SEQUENCE: 28

Leu Lys Lys Val Thr Glu Glu Met Trp Asp Pro Glu Ala Cys Ala Arg
1               5                   10                  15

Ile Thr Ala Gly Cys Ala Phe Ala Arg Val Trp Asn His
            20                  25

<210> SEQ ID NO 29
<211> LENGTH: 29
<212> TYPE: PRT
<213> ORGANISM: Xenopus laevis

<400> SEQUENCE: 29

Leu Cys Val Thr Ile Glu Glu Cys Trp Asp His Asp Ala Glu Ala Arg
1               5                   10                  15

Leu Ser Ala Gly Cys Val Glu Glu Arg Ile Ser Gln Ile
            20                  25

<210> SEQ ID NO 30
<211> LENGTH: 28
<212> TYPE: PRT
<213> ORGANISM: Human

<400> SEQUENCE: 30
```

-continued

```
Leu Lys Glu Thr Ile Glu Asp Cys Trp Asp Asp Ala Glu Ala Arg Leu
1               5                   10                  15

Thr Ala Gln Cys Val Glu Glu Arg Met Ala Glu Leu
            20                  25
```